United States Patent [19]
Shipley et al.

[11] Patent Number: 5,262,298
[45] Date of Patent: Nov. 16, 1993

[54] METHOD TO ASSESS THE ABILITY OF A SUBSTANCE TO INHIBIT OR STIMULATE KERATINOCYTE AUTOCRINE FACTOR PRODUCTION

[75] Inventors: Gary D. Shipley, Portland, Oreg.; Mark R. Pittelkow, Rochester, Minn.; Paul W. Cook, Vancouver, Wash.

[73] Assignee: The State of Oregon Acting by and Through the State Board of Education on Behalf of the Oregon Health Sciences University, Portland, Oreg.

[21] Appl. No.: 558,899

[22] Filed: Jul. 26, 1990

Related U.S. Application Data

[63] Continuation-in-part of Ser. No. 351,695, May 12, 1989, abandoned.

[51] Int. Cl.⁵ .......................... C12Q 1/68; C12Q 1/02; G01N 33/48
[52] U.S. Cl. .......................................... 435/6; 436/63; 435/29
[58] Field of Search ........................ 436/63; 435/6, 29

[56] References Cited

FOREIGN PATENT DOCUMENTS 2214185  8/1989  United Kingdom .

OTHER PUBLICATIONS

Shipley et al., *Archives of Dermatology* (1987) 123:1541a–1544a.
Shipley et al., *J. Cellular Phys.* (1989) 138:511–518.
Shipley et al., *J. Tissue Culture Methods* (1986) 10(2):117–123.
Rubin et al., *Proc. Natl. Acad. Sci.* (1989) 86:802–806.
Halper et al., *Cancer Res.* (1987) 47:4552–4559.
Masuda et al., *In Vitro Cellular & Developmental Biology* (1988) 24(9):893–899.
Masuda et al., *Cell Biology International Reports* (1987) 11(5):359–365.
Shoyab et al., *Proc. Natl. Acad. Sci.* (1988) 85:6528–6532.
Shoyab et al., *Science* (1989) 243:1074–1076.
Plowman et al., *Mol. & Cell. Biol.* (1990) 10(5):1969–1981.

Primary Examiner—Douglas W. Robinson
Assistant Examiner—Susan M. Weber
Attorney, Agent, or Firm—Morrison & Foerster

[57] ABSTRACT

Keratinocyte autocrine factor (KAF) can be isolated from human keratinocytes and is an effective and selective mitogen for keratinocytes in comparison to fibroblasts. Methods of purifying KAF using sulfated glycosaminoglycans, methods to inhibit the effect of KAF using sulfated glycosaminoglycans, and methods to assay for stimulators and inhibitors of KAF activity and production are described.

2 Claims, 19 Drawing Sheets

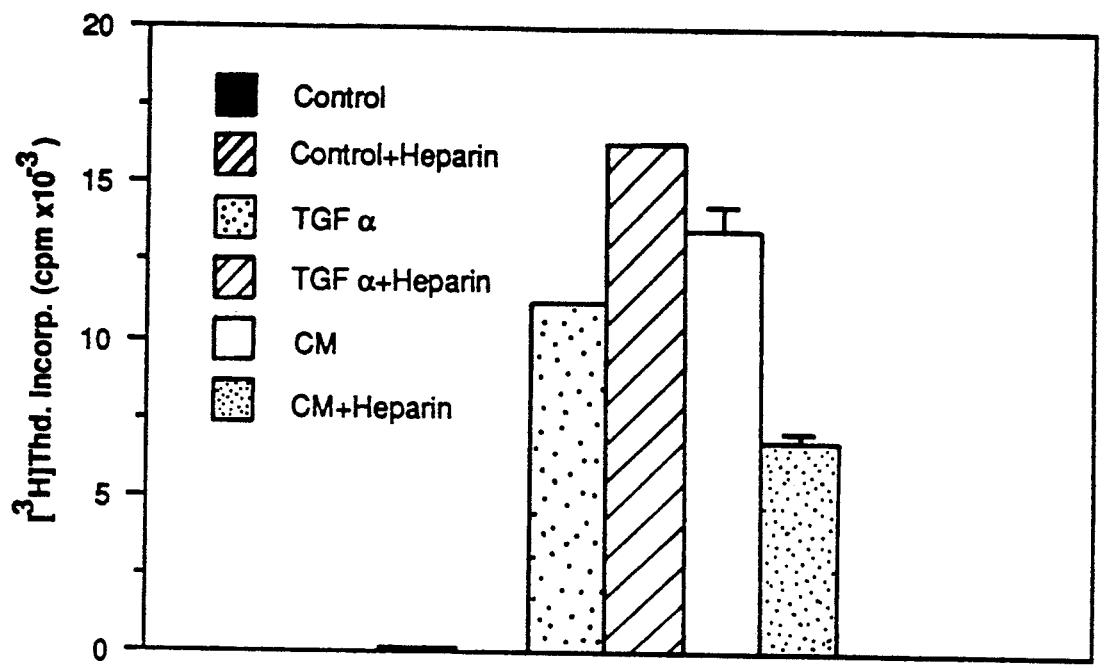
FIG. 1
FIG. 3
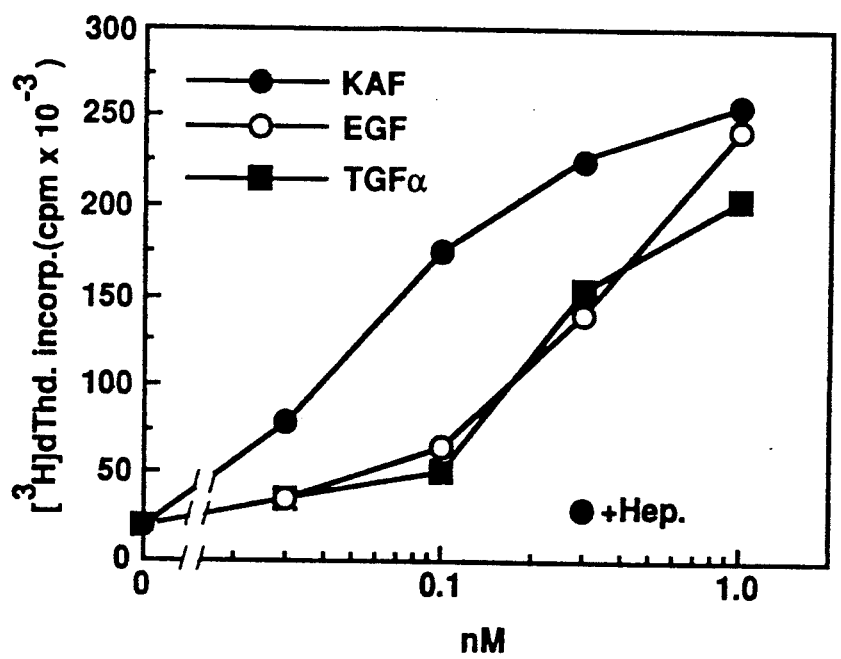

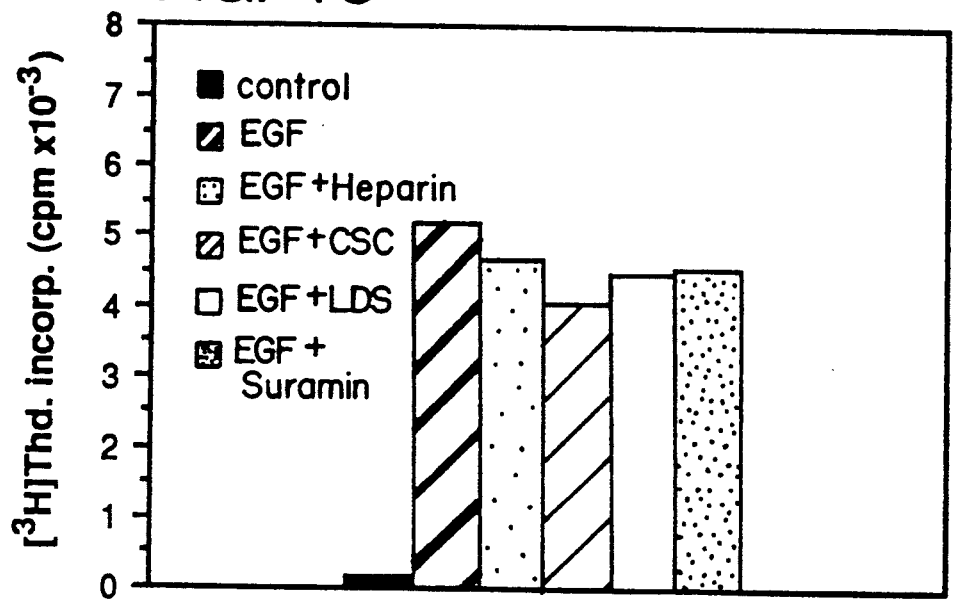
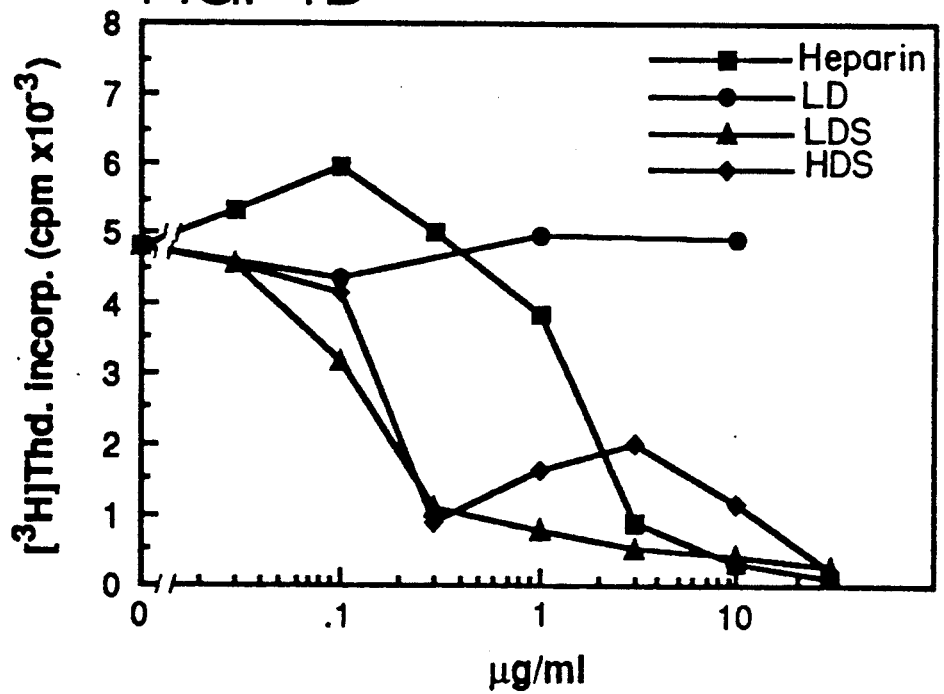

FIG. 10B
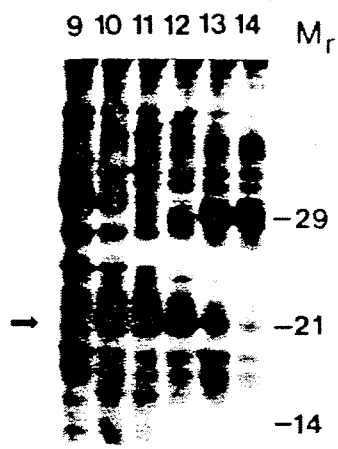
FIG. 10D
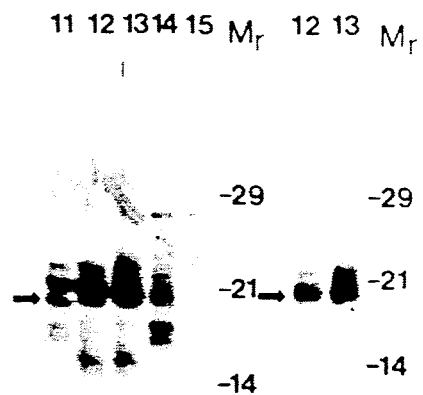
FIG. 10F  +DTT
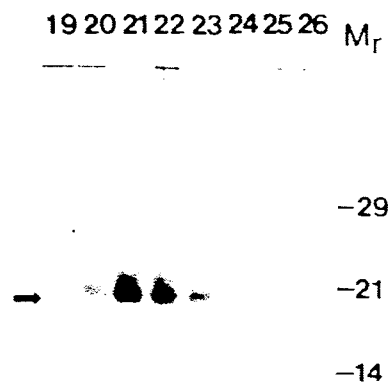

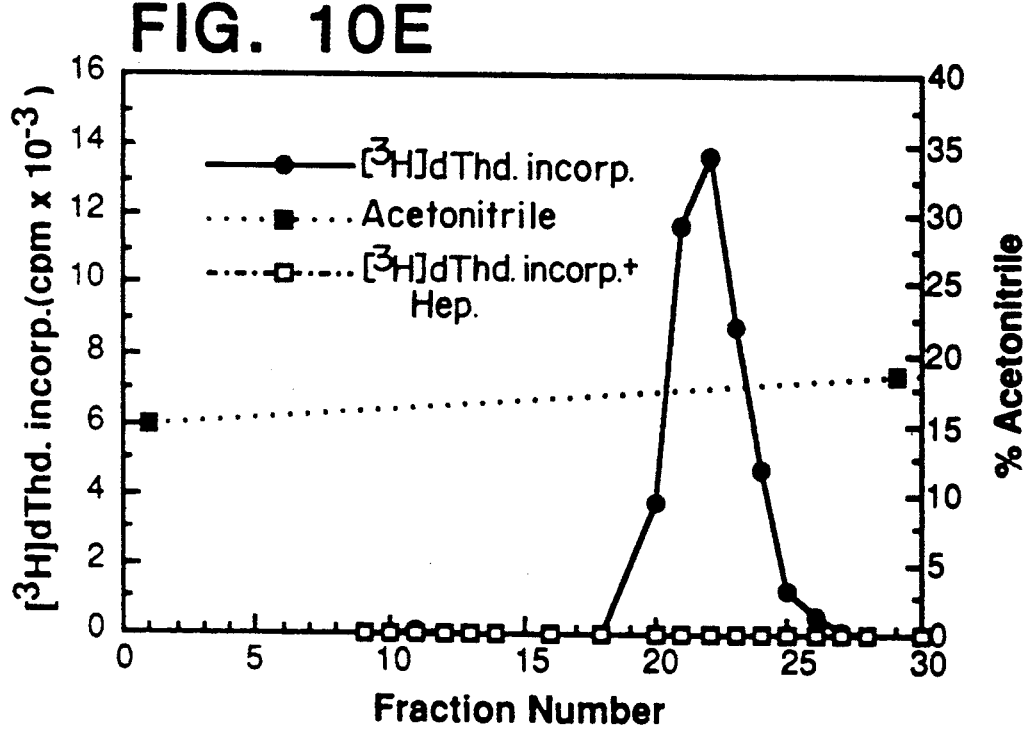

FIG. 11

|       | 1   | 2   | 3   | 4   | 5   | 6   | 7   | 8   | 9   | 10  |
|-------|-----|-----|-----|-----|-----|-----|-----|-----|-----|-----|
| KAF-1 | Ser | Val | Arg | Val | Glu | Gln | Val | Val | Lys | Pro |
| KAF-2 |     |     |     |     |     |     | Val | Val | Lys | Pro |
| AR    | Ser | Val | Arg | Val | Glu |     | Val | Val | Lys | Pro |
| AR'   | Ser | Val | Arg | Val | Glu | Gln | Val | Val | Lys | Pro |

|       | 11  | 12  | 13  | 14  | 15  | 16  | 17  | 18  | 19  | 20  |
|-------|-----|-----|-----|-----|-----|-----|-----|-----|-----|-----|
| KAF-1 | Pro | Gln | Asn | Lys | Thr | Glu | Ser | Glu | Asn | Thr |
| KAF-2 | Pro | Gln | Xxx | Lys | Thr | Glu | Ser | Glu | Asn | Thr |
| AR    | Pro | Gln | Asp | Lys | Thr | Glu | Ser | Glu | Asn | Thr |
| AR'   | Pro | Gln | Asp | Lys | Thr | Glu | Ser | Glu | Asn | Thr |

|       | 21  | 22  | 23  | 24  | 25  | 26  |
|-------|-----|-----|-----|-----|-----|-----|
| KAF-1 | Ser | Asp | Lys | Pro | Lys | Arg |
| KAF-2 | Ser | Asp | Lys | Pro | Lys | Arg |
| AR    | Ser | Asp | Lys | Pro | Lys | Arg |
| AR'   |     |     |     |     |     |     |

FIG. 12

GCACGAATTCCGTGTCCCAGAGACCGAGTTGCCCAGAGAGACCGAGACGCCGC
153
CGCTGCGAAGGACCAATGAGAGCCCGCTGCTACCGCCGGCGCCGGTGGTGC
195
TGTCGCTCTTGATACTCGGCTCAGGCCATTATGCTGTGGATTGGACCTCAATG
247
ACACCTACTCTGGGAAGCGTGAACCATTTCTGGGACCACAGTGCTGATGGAT
301
TTGAGGTTACCTCAAGAAGTGAGATGTCTTCAGGAGTGAGATTCCCCTGTGAG
355
TGAAATGCCCTTCTAGTAGTGAACCGTCCTCGGGAGCCGACTAT.........
409
                                                451
                                                1021
3' AR (antisense) primer- 3' <u>CCTCAGTGACGGTTCAGTATCGGT</u> TCGAACACG 5'

METHOD TO ASSESS THE ABILITY OF A SUBSTANCE TO INHIBIT OR STIMULATE KERATINOCYTE AUTOCRINE FACTOR PRODUCTION

This is a continuation-in-part of U.S. Ser. No. 07/351,695, filed 12 May 1989, now abandoned.

TECHNICAL FIELD

The invention relates to growth factors which are mitogenic in epidermal cells. More specifically, the invention concerns an autocrine growth factor secreted by keratinocytes capable of ameliorating pathological conditions such as skin lesions.

BACKGROUND ART

Keratinocytes are the major cell type in the epidermis, a multilayered group of cells without blood vessels on the surface of the skin. Presumably, proliferation and growth of epidermal cells in vivo is nourished by nutrients from the dermal layer, including growth factors. Keratinocytes have been propaged in vitro in continuous culture using defined medium for example as described in Shipley, G.D., et al., *Arch Dermatol* (1987) 123:1541A–1544A. The medium contains various inorganic ions. trace elements, amino acids, vitamins and other organic compounds and is not qualitatively different from defined media used to culture other mammalian cell lines. In this publication it was noted that insulin and epidermal growth factor (EGF) were required for clonal growth in vitro and that hydrocortisone was beneficial.

Basic fibroblast growth factor (bFGF) is able to replace EGF in supporting the clonal growth of keratinocytes in a dose-dependent manner; acidic fibroblast growth factor (aFGF) is also a potent mitogen (Shipley, G.D., et al., *J Cell Physiol* (1989) 138:511–518, incorporated herein by reference). These FGFs are members of a class of heparin-binding growth factors (HBGF) which includes the products of several potential oncogenes. The ability of bFGF to stimulate proliferation of keratinocytes is inhibited by heparin; heparin has no effect on stimulation by EGF or TGFa and only minimal effect on stimulation by aFGF.

It is also known that transforming growth factors (TGF) are produced by virally transformed cells and tumor cell lines. These factors stimulate soft agar colony formation of cells that are normally anchoragedependent and cause the overgrowth of these cells in a monolayer culture. Two major classes of transforming growth factors have been identified—TGF—alpha and TGF—beta. Other growth factors including platelet-derived growth factor (PDGF) and HBGFs also can contribute to anchorage-independent growth of some target cells. Shipley, G.D., *J Tissue Culture Methods* (1986) 10:117–123, describes a simple in vitro serum-free thymidine-incorporation assay for detection of transforming growth factors.

A purified factor from fibroblasts designated keratinocyte growth factor (KGF) was described by Rubin, J.S., et al., *Proc Natl Acad Sci USA* (1989) 86:802–806. This factor is labile to acid treatment and stable to reduction. Other growth factors which have been described are transforming growth factor type-e (Halper et al., *Cancer Res* (1987) 47:4552–4559), and DNA synthesis factor (Masuda et al., *In Vitro Cell and Devel Biol* (1988) 24:893–899; Masuda et al., *Cell Biol Int Rep* (1987) 1:359–365).

Shoyab, M., et al., *Proc Natl Acad Sci USA* (1988) 85:2528–2532, described a glycoprotein which they termed amphiregulin (AR) which inhibits the growth of human carcinoma cells in culture but stimulates proliferation of human fibroblasts and other tumor cells. Amphiregulin was obtained from serum-free conditioned medium of the MCF-7 cell line derived from a human breast carcinoma which was stimulated with phorbol 12-myristate 13-acetate. Unlike keratinocyte growth factor (KGF), AR was not acid labile and the foregoing report indicated that the glycosylation could be removed but activity retained, and the N-terminal sequence was disclosed. In a subsequent paper, Shoyab, M., et al., *Science* (1989) 243:1074–1076, the complete amino acid sequence of a "truncated" form containing 78 amino acids as determined using protein-sequencing techniques as well as a larger form containing 6 additional amino acid sequences at the N-terminal end was reported. It was further disclosed that amphiregulin binds to the EGF receptor but less strongly than does EGF itself. Amphiregulin was shown to stimulate the growth of the murine keratinocyte cell line Balb/MK and could supplant the EGF requirement in these cells. In these assays, the keratinocytes were plated at $10^4$ cells per well and cultured overnight to a starting cell density of approximately $10^4$ cells/cm$^2$.

In a more recent publication, Plowman, G.D., et al., *Mol Cell Biol* (1990) 10:1969–1981, this same group reported the cloning of the gene encoding the 252 amino acid precursor of the 84 amino acid amphiregulin "mature" peptide secreted by MCF-7 cells, which precursor had an organization similar to the transmembrane precursor corresponding to TGF-alpha. Human placenta and ovaries also were reported to express significant amounts of the AR transcript. Assessment of the biological activity of the amphiregulin was not elaborated over that of the Science paper which had shown only data that AR had stimulatory activity with respect to murine keratinocytes under the high cell density conditions of the reported assay. These cells do not make KAF.

The reported amino acid sequence of amphiregulin matches that of the keratinocyte autocrine factor of the present invention. These data are also the subject of published British application GB2214185A, published 31 August 1989.

Two types of models have been described to account for the loss of growth control in tumor cells. In one, the "autocrine hypothesis," the production of and response to a growth factor by the same cells, leading to an increase in proliferation rate of these cells, is postulated. In an alternative "paracrine hypothesis," secretion of factors by the tumor cells are thought to stimulate the production of growth factors by surrounding tissues, which, in turn, stimulate the growth of the tumor cells.

In short, while the process whereby cells are permitted to proliferate in vivo and in vitro is far from understood, it is known that there is a complex interrelationship of growth factors, which in some way regulates this proliferation. The present invention relates to an autocrine factor selective for the proliferation of keratinocytes.

DISCLOSURE OF THE INVENTION

It has been found that keratinocytes, when plated at higher than $10^3$ cells/cm$^2$, can be grown without supplementation with polypeptide growth factors, thus suggesting the autocrine stimulation of proliferation by self-secreted growth factors (Shipley, G.D., et al., *J Cell Physiol* (1989) 138:511-518 (supra), incorporated herein by reference). One of these growth factors, designated keratinocyte autocrine factor herein (KAF), binds to heparin and can be purified by heparin affinity chromatography.

Thus, in one aspect, the invention relates to methods to purify keratinocyte autocrine factor which comprise contacting a sample containing the KAF to be purified with a suitable sulfated glycosaminoglycan (GAG) or carbohydrate immobilized to a solid support under conditions wherein the KAF is adsorbed. The adsorbed KAF is then eluted from the solid support, preferably in an elution protocol wherein a number of fractions are obtained, only some of which contain KAF.

In another aspect, the invention is directed to a method to inhibit the mitogenic effect of KAF on responsive cells either in vivo or in vitro by taking advantage of the inhibitory effect of certain sulfated glycosaminoglycans and carbohydrates on KAF. For in vitro inhibition, the sulfated GAG or other sugar may be added directly to the cell culture; for in vivo inhibition, the inhibitor is administered to the subject to minimize the mitogenic effect of endogenous KAF.

The invention also relates to methods to identify stimulators and inhibitors of KAF activity and KAF production. To assess regulation of KAF activity, candidate substances are added to KAF-treated cultures of cells responsive to KAF, such as AKR-2B cells in serum free medium and their effect on indices of growth, such as labeled thymidine incorporation, is measured. This assay is conducted in the presence and absence of heparin or other sulfated carbohydrate inhibitor to isolate the response due to KAF. For stimulators and inhibitors of KAF production, candidate substances are added to culture media for KAF-producing cells and their effect on KAF mRNA and/or protein is measured.

In still other aspects, the invention is directed to a method to produce KAF by culturing human keratinocytes or mammary epithelial cells under conditions which favor KAF production and recovering the KAF produced, preferably by heparin affinity chromatography.

In still other aspects, the invention is directed to the use of KAF to minimize scarring in surface wounds by taking advantage of the selective mitogenic effect of KAF on keratinocytes in comparison to fibroblasts. In still another aspect, the invention relates to methods to grow keratinocytes from low density in culture by enhancing their growth with KAF, and to drug delivery systems which depend on slow release of KAF from sulfated carbohydrates.

The invention also relates to keratinocyte autocrine factor itself in purified and isolated form, to recombinant materials and methods for its production, and to antibodies immunoreactive with this protein or glycoprotein.

BRIEF DESCRIPTION OF THE DRAWINGS

FIG. 1 shows the effect of heparin on the activity of TGF-alpha and of conditioned medium from human keratinocytes on AKR-2B, cells.

—FIG. 2A shows the effect of heparin on TGF-alpha and purified KAF; FIG. 2B shows the effect of heparin on the mitogenic activity of acidic and basic FIG.

FIG. 3 shows the effect of various growth factors on thymidine incorporation by MK-2 cells.

FIG. 8a shows its effect on normal human fibroblasts; FIG. 8b shows the effect of KAF on AKF-2B cells; and FIG. 8c shows its effect on EGF-receptorless mouse NR-6 cells.

FIGS. 10A, 10C, and 10E show elution patterns from various steps in the purification of KAF and FIGS. 10B, 10D, and 10F show results from electrophoresis indicating its purity.

FIG. 11 shows the N-terminal amino acid sequences of the two forms of KAF protein obtained from keratinocyte conditioned media in comparison to the N-terminal sequences of amphiregulin.

FIG. 12 shows the nucleotide sequence of DNA obtained using the PCR reaction from human keratinocyte RNA.

MODES OF CARRYING OUT THE INVENTION

Figure 2A:
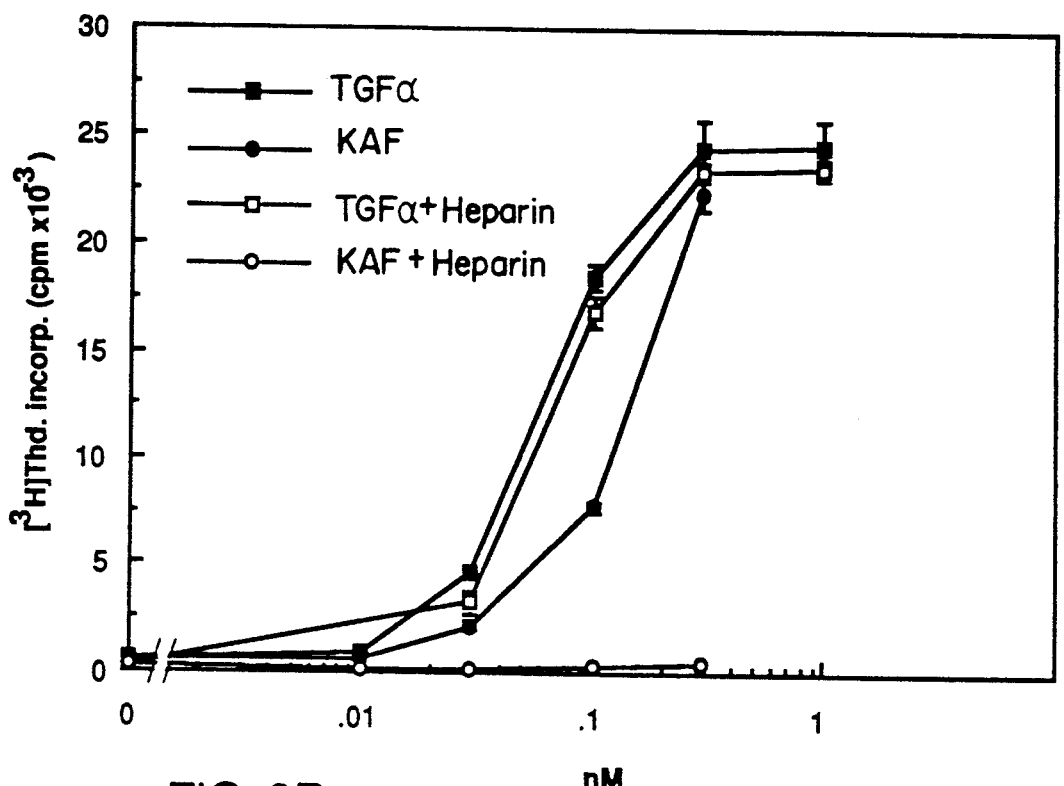
FIGS. 2A and 2B shows the effect of heparin on the mitogenic ability of a number of growth factors on AKR-2B cells

The invention relates to keratinocyte autocrine factor (KAF) which is produced by human keratinocytes and mammary epithelial cells. This protein, while similar to amphiregulin referenced above, has a number of properties undisclosed in the art which result in methods and materials useful in diagnosis and therapy. Notable among these are the following:

1. The inhibition of KAF activity by heparin sulfate permits the isolation of effects of KAF activity in a manner that distinguishes them from those of other growth factors. Thus, assays designed to measure cell growth can be made specific for KAF by running them in the presence and absence of heparin sulfate. The assays can be used to determine suitable substitutes for heparin inhibition such as other inhibitory sulfated glycosaminoglycans or sugars. The growth stimulating activity exhibited in the absence of heparin (or other specific inhibitor) minus that exhibited in the presence of heparin is attributable to KAF specifically, and not to other growth factors which would otherwise interfere, such as TGF-alpha. The availability of this specific assay for KAF permits systematic determination of which among candidate substances are capable of stimulating and which inhibiting the effect of KAF, as well as a convenient assay method for use in following KAF purification. Thus, the assay specific for KAF is also useful in identifying KAF-containing fractions during purification procedures designed to isolate this protein. KAF stimulating and inhibitory factors are useful in therapeutic applications associated with conditions characterized by excessive or inadequate KAF activity, as further described below.

2. The ability of heparin and other sulfated carbohydrates to bind KAF also provides a convenient tool for isolation and purification of this protein from natural sources or from recombinant cells in which it is produced. Use of the appropriate sulfated carbohydrates as affinity ligands bound to solid supports permits the use of specific affinity chromatography or batchwise adsorption and elution to isolate KAF.

3. Also because KAF binds sulfated heparin and other sulfated carbohydrates, drug delivery systems which provide a matrix which specifically binds KAF can be designed to effect slow and controlled delivery of KAF.

4. Inhibitors of KAF are useful in the control of hyperproliferative diseases as outlined further below. All of the compounds found by the invention assay to inhibit KAF mitogenic activity can be used in this way as further described herein. However, it is also known from FIGS. 5 and 6 that heparin, and presumably alternate sulfated carbohydrates, are capable of inhibiting the growth of keratinocytes regardless of the mechanism thereof. Thus, compounds which merely are shown by the assays carried out in Example 1 below are useful in such treatment protocols.

5. Because KAF is an autocrine factor, it can be used to enhance the growth of clonal cells in culture starting at low cell densities such as those that would be used in preparing artificial skin for grafting. Although amphiregulin has been reported to support the growth of mouse keratinocytes, the disclosures presently in the art report only the stimulation of Balb/c MK-cells—cells which have been shown by the applicant not to produce KAF. Furthermore, KAF fails to stimulate the growth of these cells at clonal density. The ability of KAF to stimulate the growth of human keratinocytes and mammary epithelial cells from clonal densities permits the use of this substance to prepare skin in culture.

6. Also because KAF is an autocrine factor, stimulators and inhibitors of its production can be identified by testing the effect of candidate substances on the production of KAF mRNA and/or protein in human keratinocyte cell cultures.

7. It has also been determined that KAF is significantly more effective in stimulating the growth of keratinocytes than in stimulating the growth of fibroblasts. As fibroblasts are responsible for the scarring observed in wound healing, KAF is a particularly advantageous material for use on surface wounds and abrasions which otherwise involve the formation of large amounts of scar tissue.

The paragraphs below describe the methods and compositions which are useful as a result of these newly disclosed properties of KAF.

SPECIFIC ASSAYS FOR KAF ACTIVITY

Figure 2B:
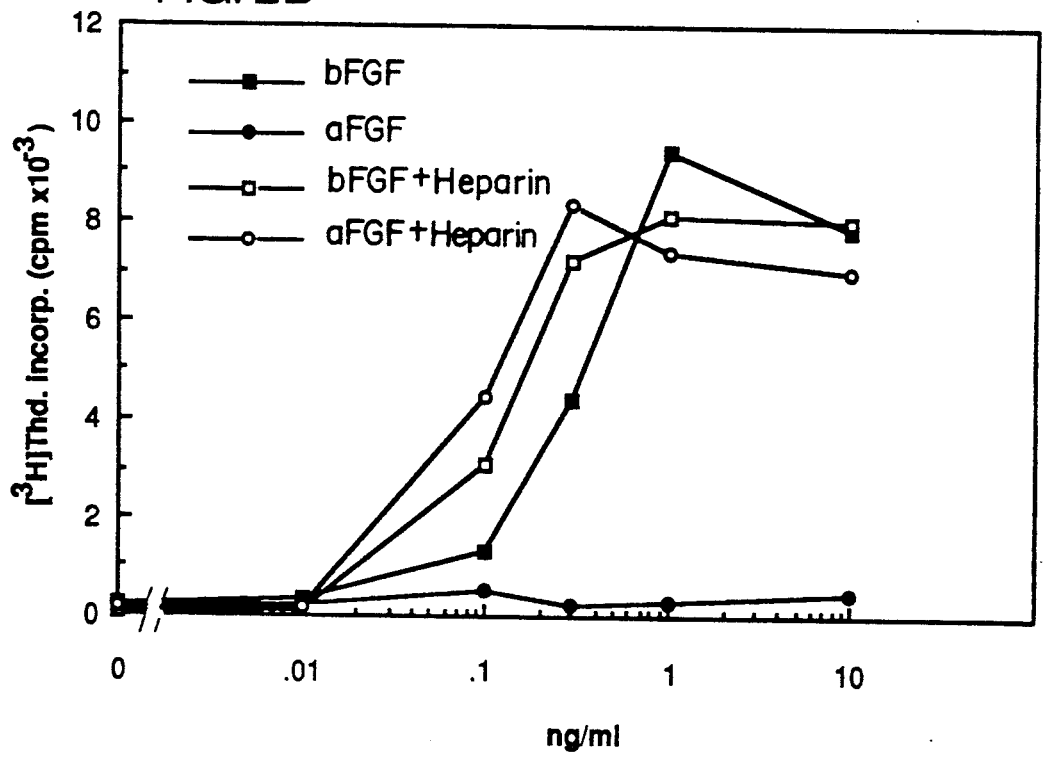

Because of the unique property of KAF associated with its inhibition by heparin sulfate or other sulfated carbohydrates, growth assays can be made specific for KAF. In particular, we have demonstrated that the use of AKR-2B cells in a mitogenic assay can be used for the specific detection of KAF activity, including its application to track the purification of KAF from complex mixtures of growth factors. The mitogenic activity of crude keratinocyte conditioned medium in this assay is only partially inhibited by the addition of heparin sulfate indicating that both heparin-inhibitable and non-heparin-inhibitable growth factors are present in this conditioned medium (FIG. 1). When this material is bound to a heparin-acrylamide column and then eluted with a NaCl gradient and samples tested in the AKR-2B cell assay in the presence and absence of heparin sulfate (10 ug/ml), active fractions which are inhibited by heparin are indicative of KAF activity. Other EGF-like factors (TGF-alpha or EGF) do not have this property, as shown in FIG. 2A, nor do other heparin-binding growth factors such as aFGF or bFGF (FIG. 2B); the activity of aFGF is markedly stimulated by heparin. FIG. 3 summarizes analogous results for MK-2 cells which could thus be used in a similar fashion to detect KAF activity and distinguish this activity from that of other growth factors. As seen in FIG. 3, heparin also diminishes greatly the growth of MK-2 cells stimulated by KAF.

Thus, the specific assay for KAF in general depends on using as substrate cells responsive to stimulation by KAF. Such cells include human keratinocytes at clonal densities, AKR-2B cells, MK-2 cells, and the like. Growth is assessed at suitable concentrations of growth factor by measurement of typical indicators of growth, such as labeled thymidine incorporation, colony formation and increased cell number. Matching concentrations are run in the presence of a suitable inhibitory sulfated carbohydrate such as heparin sulfate. Since this ability is known for heparin sulfate, the assay described in AKR-2B cells described above, for example, can be used to determine other appropriate sulfated GAG or sulfated sugar inhibitors of KAF mitogenic activity. The results of such an assay are shown in FIG. 4.

Figure 4A:
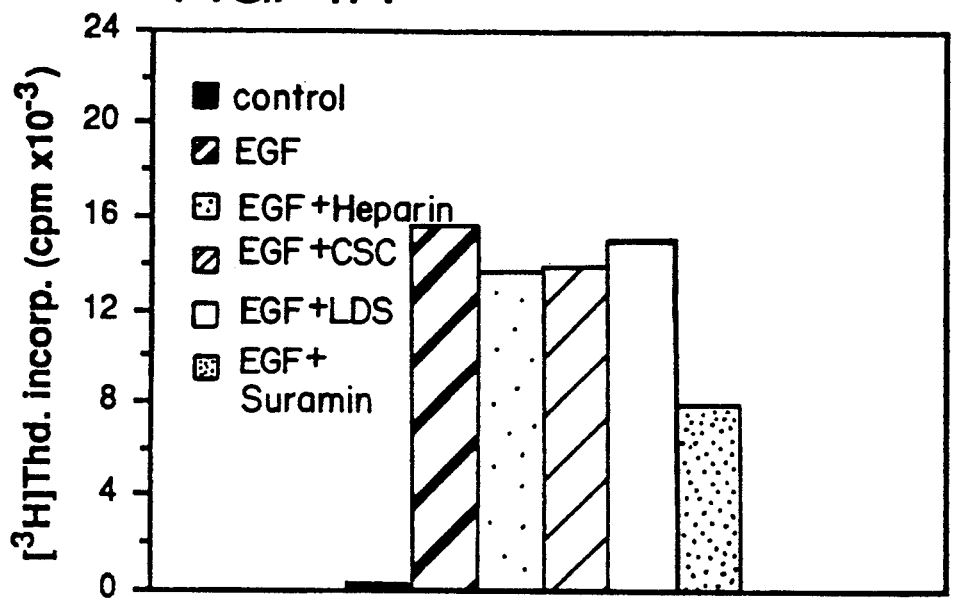
FIGS. 4A and 4B show the results of an assay to determine candidate inhibitors of KAF activity and FIGS. 4C and 4D compare those KAF inhibitor candidates on the activity of EFG.
Figure 4B:
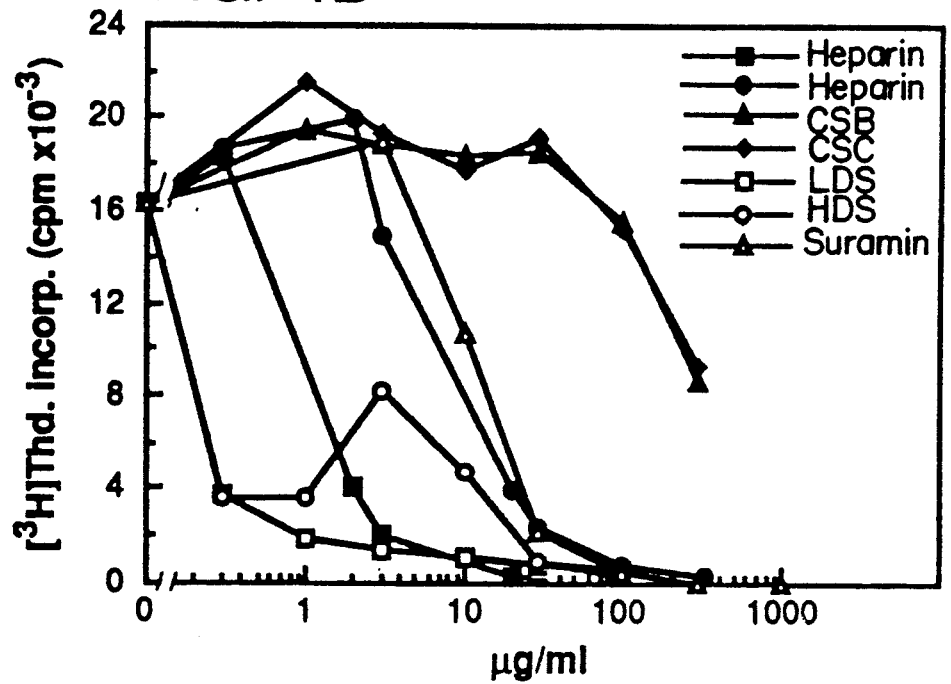

As shown in FIGS. 4A to 4D when AKR-2B cells are stimulated by KAF in the presence of 500 ng/ml insulin, sulfated compounds such as heparin, heparan, low molecular weight dextran sulfate (LDS) and high molecular weight dextran sulfate (HDS) are potent inhibitors of KAF activity (FIGS. 4B and 4D) but not the EGF activity shown in FIGS. 4A and 4C (EFG=2 ng/ml; test compounds at concentrations that are maximally inhibitory for KAF). Compounds such as chondroitin sulfate B (CSB) and chondroitin sulfate C (CSC) which are also sulfated are not nearly as effective. Nonsulfated low molecular weight dextran (LD) has no effect on KAF activity indicating that the sulfation is essential for KAF inhibition.

The following describes an illustrative protocol for the use of target cells with and without addition of heparin sulfate or other sulfated GAG or carbohydrate to assess candidate compounds for their ability to stimulate or enhance KAF activity specifically. Of course, this assay can be modified by using other cells known to be responsive to KAF, such as MK-2 cells, human keratinocytes, and mammary epithelial cells; by using other methods of detection of growth, and by using alternate specific inhibitors of KAF activity. The illustrative steps in such an assay are as follows:

1. AKR-2B or a subclone derived from these cells (E11A3) are plated in multiwell dishes at a concentration of $5 \times 10^3$ cells/cm$^2$ in medium McCoy's 5A supplemented with 5% FBS and grown to confluence over a 5 day period.

2. The medium in the wells is changed to medium MCDB 402 (Shipley and Ham In Vitro (1981) 17:656–670) without additional supplementation and the cells are incubated for an additional 48 hours.

3. The medium is changed to fresh medium MCDB 402 supplemented with 500 ng/ml insulin. For the detection of KAF mitogenic activity, samples suspected of containing KAF are added at appropriate concentrations with and without additional supplementation with 10 ug/ml heparin sulfate. Control wells receive 10 ng/ml EGF with and without 10 ug/ml heparin sulfate. The enhancement of tritiated thymidine incorporation in the wells lacking heparin sulfate over those in which heparin sulfate is present is a measure of KAF activity.

4. For detection of potential KAF stimulating and inhibiting compounds, KAF as determined above is added at concentrations between 0.01 and 10 nM such that the resultant stimulation is approximately ½ maximal to just maximal. EGF and/or other control growth factors (such as bFGF and/or aFGF) are added to control wells at similar concentrations. Varying concentrations of putative inhibitors are then added and the cultures are incubated at 37° C.

5. After an additional 22 hours of incubation, 1.0 uCi/ml 3H-deoxythymidine (50–80 Ci/mMol) is added in a small volume and the cultures incubated for 1 hour at 37° C. The relative amount of incorporated label is then determined as described in Shipley, *J Tiss Cult* (1986) 10:117–123, incorporated herein by reference, or by other common methods.

Use of Human Keratinocytes to Detect Agents That Have the Ability to Regulate Endogenous Production of KAF Human keratinocytes isolated from fetuses, newborn or adult skin and grown in culture, or cell lines derived from these sources may be utilized for identification of agents that regulate KAF production at the transcriptional, post-transcriptional, translational or post-translational processing steps. The cells can be isolated utilizing a number of techniques including those described in Wille, et al. (*J Cell Physiol* (1984) 121:31–44) and grown as described in Shipley et al. (*J Cell Physiol* (1989) 138:511–518), or other suitable serum-free formulations of medium MCDB 153 such as the commercially available medium KBM (Clonetics Corp., San Diego, CA) for stock culture propagation. KBM is modified MCDB 153 medium containing $1 \times 10^{-4}$ M ethanolamine, $1 \times 10^{-4}$ M phosphoethanolamine, and higher amino acid concentrations as described in Pittelkow et al., Mayo Clin Proc (1986) 61:771–777.

For determinations of KAF-production regulating materials, cells from primary, secondary or tertiary culture of normal keratinocytes or keratinocyte-derived cell lines are removed from the stock culture flasks with trypsin/EDTA, resuspended in medium supplemented with 0.5% FBS, centrifuged and resuspended in medium KGM. KGM is KBM medium (described above) supplemented with 0.4% bovine pituitary extract (BPE), EGF, insulin and hydrocortisone by the manufacturer. The cells are plated at a suitable density for the particular assay (between $1 \times 10^3$ and $5 \times 10^4$ cells/cm$^2$) and incubated overnight in a cell culture incubator. The following morning, the medium is removed and replaced with medium KBM supplemented with $5 \times 10^{-7}$ M hydrocortisone or the same medium supplemented with hydrocortisone and 5.0 ug/ml insulin. The incubation is continued for a suitable time to allow the cells to achieve a steady state of growth (usually 2-3 days should be sufficient).

Candidate agents to be assessed for their ability to modify the production of KAF are added with fresh medium over a range of concentrations and the production of KAF mRNA and/or protein is measured over time. Methods for monitoring KAF mRNA levels include but are not limited to: Northern blot, solution hybridization, RNAse protection, and/or quantitative polymerase chain reaction techniques. Methods for monitoring KAF protein include but are not limited to: Western blot, immunoprecipitation, radioimmunoassay, ELISA, AKR-2B cell thymidine incorporation assay, $^{125}$I-EGF binding assay and/or MK-2 cell thymidine incorporation assay techniques.

Thus, by using the production of KAF mRNA or protein in keratinocytes as a criterion, stimulator and inhibitors of KAF production can be identified.

Use of KAF and/or Agents That Regulate KAF Activity and/or Production in Therapy KAF is an autocrine growth factor for human keratinocytes and, thus, is an important regulator of keratinocyte proliferation and differentiation in vivo. Aberrant production of KAF may be involved in pathological states in human skin and the epithelium of other tissues. Regulation of KAF production and/or activity can be used therapeutically to treat conditions which are caused or abetted by too much or too little KAF activity or production.

Conditions which would benefit by administration of KAF or of stimulators of its production and/or activity include: lupus erythematosus; corticosteroid-induced atrophy; pemphigus, pemphigoid; epidermal thinning associated with aging; epidermal ulcerations, including decubitius ulcers, ischemic ulcers, infarctive ulcers, vascular ulcers, and hemoreologic ulcers; androgenetic alopecia; and alopecia areata.

Conditions which would benefit by administration of an inhibitor of KAF activity and/or production include: psoriasis; pityriasis rubra pilaris; acanthosis nigricans; ichyosis; exfoliative dermatitis; erythrokeratoderma variabilis, Dariers disease; as well as squamous cell carcinomas—especially of the skin, lung and urogenital tract; adenocarcinomas—especially of the breast; and basal cell carcinomas of the skin.

In skin disease states characterized by hypoactivity or hypoproduction of KAF, the application of KAF or agents which cause stimulation of its activity in a suitable cream or other type of salve will be effective in ameliorating the condition. In addition, pharmaceutical agents which can increase the production of endogenous KAF by keratinocytes and cells derived from keratinocytes in hair follicles will be effective in the treatment of these conditions.

In the conditions characterized by an excess of KAF activity, the application of agents that inhibit the biological activity of KAF such as heparin sulfate and dextran sulfate or other compounds as described herein, or other KAF inhibitors which can be identified using the assays described above will be effective in treatment of these conditions. Likewise, the treatment of these conditions with pharmaceutical agents shown to inhibit the endogenous production of KAF by keratinocytes will be effective in ameliorating these conditions.

KAF is useful in the treatment of skin abrasions, burns and other epidermal wounds such as bedsores and burns. The cell-type specificity of KAF in stimulating keratinocytes at lower concentrations than that required for fibroblasts as shown below is crucial for its use as an epidermal healing agent when incorporated into dressings for bandages or applied directly to the surface in a salve or cream.

For use in treatment, the KAF is formulated using standard pharmaceutical excipients suitable to its mode of administration. Typically, the administration will be topical, and therefore formulations into ointments, creams, solutions, gels, and lotions are preferred. Typical formulations for such compositions are found in *Remington's Pharmaceutical Sciences*, Mack Publishing Co., Easton, Pa, latest edition.

The KAF is formulated to comprise appropriate amounts of the compositions according to the nature of the excipient and the nature of the lesion or condition being treated. Suitable dosage levels depend on a number of well-known factors, and can be optimized using standard methods known in the art.

KAF-Delivery Systems

For the delivery of KAF to any site in the body, and in particular for application of KAF or any derivatives of KAF to the body surface, reversible binding of KAF to immobilized supports and/or immobilized supports incorporated into bandages is advantageously effected by immobilization of sulfated compounds which bind KAF with high affinity such as heparin sulfate, dextran sulfate or sulfated carbohydrates or other compounds which can be identified by the techniques described herein. When bound to such immobilized supports the growth factor is in an inactive state and the matrix acts as a continuous source of active KAF as the growth factor is slowly released.

Use of KAF for Propagation of Cells in Vitro

KAF is useful for the propagation of keratinocytes in culture; for the selective growth of keratinocytes from mixed populations of cells (especially mixed populations containing fibroblasts); for the growth of keratinocytes in vitro for the purpose of autografting and allografting these cells in the treatment of burns or skin lesions using techniques such as those described (Pittelkow et al., *Mayo Clin Proc* (1986) 61:771–777). The condition for clonal growth of cells using KAF are set forth in the Examples below.

Use of Heparin Sulfate as an Affinity Support in KAF Purification

The examples below illustrate the use of heparin sulfate and other sulfated carbohdrates, such as heparan sulfate and dextran sulfate in the purification of KAF from biological samples. The techniques employed are otherwise standard in the art, including the ligation of the binding affinity ligand to a solid support and application of chromatographic techniques, both fractionation and batch-wise separations.

Recombinant Production of KAF

Provision of a suitable DNA sequence encoding the desired protein KAF permits the production of the protein using recombinant techniques now well known in the art. The coding sequence can be obtained by retrieving a cDNA or genomic sequence from a native source of the protein or can be prepared synthetically using the accurate amino acid sequence found by careful protein sequencing and/or deducing the amino acid sequence from the nucleotide sequence of the gene. When the coding DNA is prepared synthetically, advantage can be taken of known codon preferences of the intended host.

Expression systems containing the requisite control sequences, such as, promoters, and preferably enhancers and termination controls, are readily available and known in the art for a variety of hosts.

Thus, the desired proteins can be prepared in both procaryotic and eucaryotic systems, resulting, in the case of many proteins, in a spectrum of processed forms. The most commonly used procaryotic system remains *E. coli*, although other systems such as *B. subtillis* and Pseudomonas could also be used. Suitable control sequences for procaryotic systems include both constitutive and inducible promoters including the lac promoter, the trp promoter, hybrid promoters such as the tac promoter, and the lambda phage $P_l$ promoter. In general, foreign proteins may be produced in these hosts either as fusion or mature proteins; when the desired sequences of KAF are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in procaryotic hosts in this manner, the signal sequence is removed upon secretion.

A wide variety of eucaryotic hosts is also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to process introns which may occur in the genomic sequences encoding proteins of higher organisms, such as KAF. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers. As above, promoters can be either constitutive or inducible. For example, in mammalian systems, the MTII promoter can be induced by the addition of heavy metal ions.

The particulars for the construction of expression systems suitable for desired hosts are well known to those in the art. For recombinant production of the KAF protein, the DNA encoding it is suitably ligated into the expression system of choice, and the system is then transformed into the compatible host which is then cultured and maintained under conditions wherein expression of the included gene takes place. The protein thus produced is recovered from the culture, either by lysing the cells or from the culture medium as appropriate.

Antibody Production

Antibodies may be prepared to the KAF of the invention using standard immunization protocols. The protein is injected into suitable hosts such as rabbits, mice, rats or sheep usually in the presence of an adjuvant. Immunization with the protein is repeated until high titers of antibodies appear in the serum. The polyclonal serum provides a source of antibodies satisfactory for some applications; however, immortalized cells which secrete monoclonal antibodies immunoreactive with the protein may be prepared using standard techniques from the spleen or peripheral blood lymphocytes of the immunized animal. The resulting immortalized cells can be cultured in vitro to obtain a reproducible source of antibody, or may be injected into, for example, mice, and the antibodies harvested from ascites fluid.

The following examples are intended to illustrate but not to limit the invention.

EXAMPLE 1

Secretion of KAF

Figure 5:
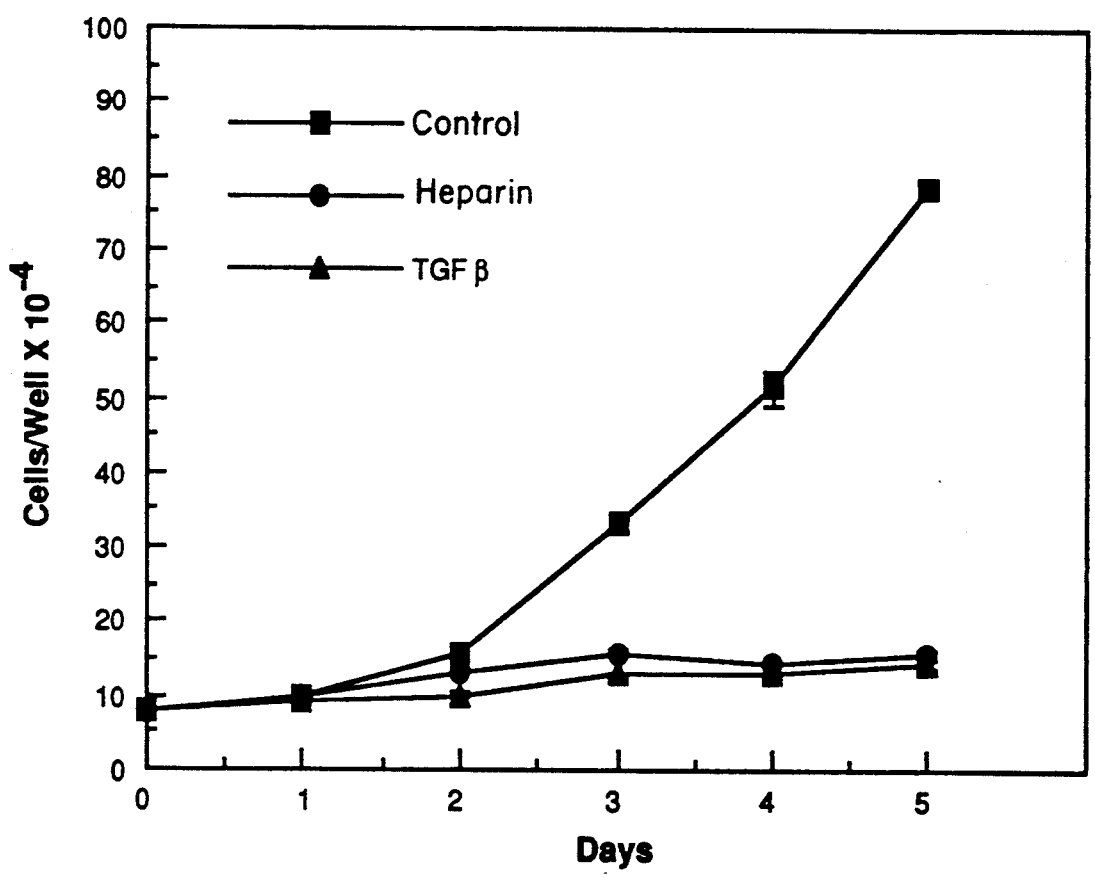
FIG. 5 shows a plot of growth of keratinocytes starting from a $10^4$ cells/cm$^2$ density in the presence and absence of heparin.

Keratinocytes were grown in the defined medium KBM supplemented with $5 \times 10^{-7}$ M hydrocortisone and 5 ug/ml insulin in the absence of EGF at an initial concentration of $1.0 \times 10^4$ cells/cm$^2$. As shown in FIG. 5, without the addition of heparin (squares) growth is rapid after an initial lag phase. However, heparin added at 10 ug/ml in the original culture (circles) results in complete inhibition of proliferation; as does the addition of TGF-beta (triangles) used as a control.

Figure 6:
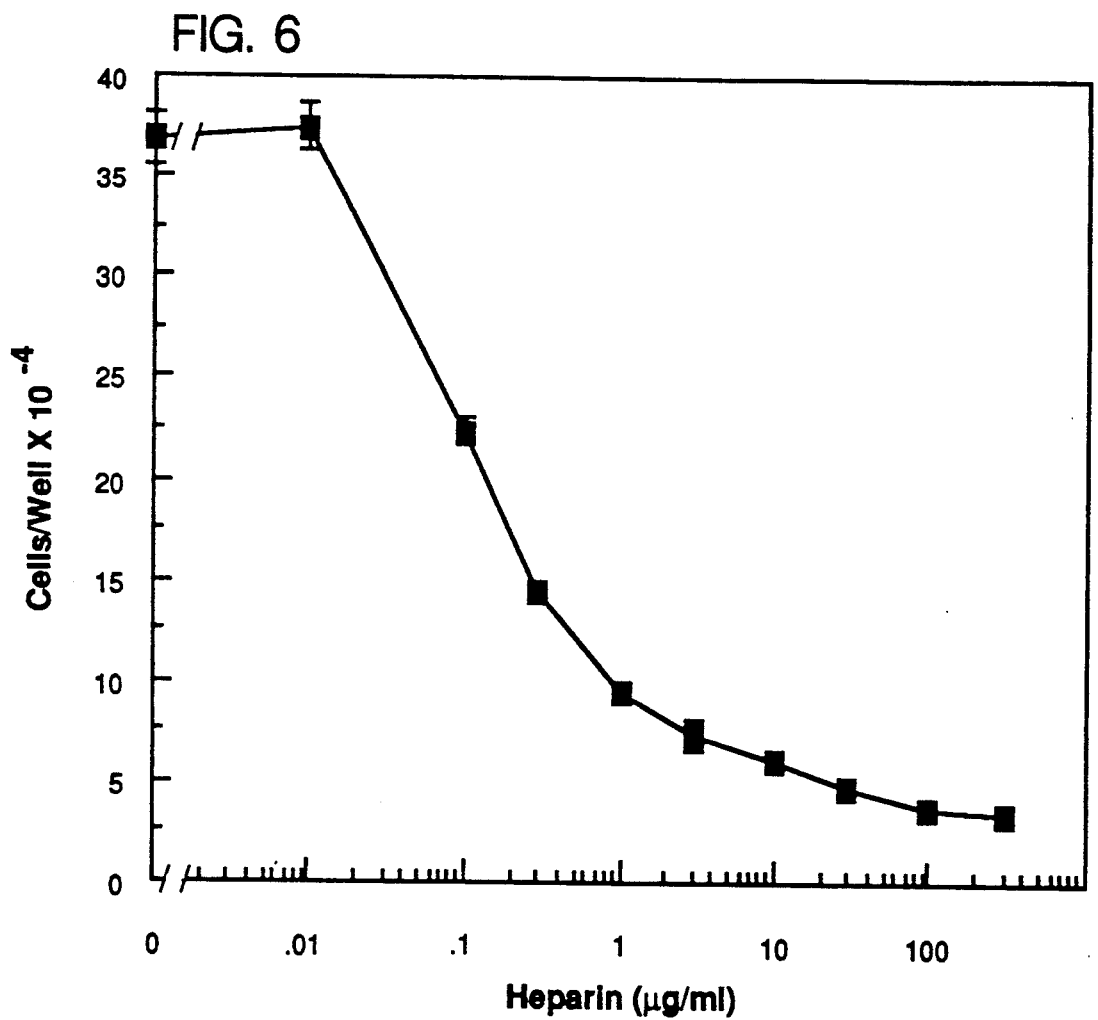
FIG. 6 shows the effect of heparin on cell count under the conditions of FIG. 5.

Cells were cultured at various levels of heparin in the same manner as described for FIG. 5 and growth was measured after 5 days with the results shown in FIG. 6. At 1 ug/ml heparin, growth was almost completely inhibited; half maximal growth inhibition occurred at 0.1 ug/ml, and inhibition was dose-dependent between 0.01 and 100 ug/ml.

EXAMPLE 2

Partial Purification of KAF

Keratinocytes were plated in KGM medium at a density of $2.5 \times 10^3$ cells/cm2 in 100 mm tissue culture dishes. After 48 hours incubation the cells were fed fresh medium and 24 hours later the cells were washed 3 times in a HEPES buffered saline solution ("Solution A," Shipley and Ham, In Vitro (1981) 17:656-670) and subsequently cultured for 24 hours in KBM medium supplemented with $5 \times 10^{-7}$ M hydrocortisone (standard medium). The medium was then replaced with fresh standard medium.

Keratinocyte conditioned medium was thereafter collected every 24 hours for 4-5 days until the cells reached 90-100% confluency. Keratinocyte conditioned medium (4.2 L) was frozen at $-80°$ C. and later thawed and pooled for concentration. Concentrate was 43-fold at 4° C. using a Millipore Minitan concentrator utilizing 10,000 kd cutoff filters.

Concentrated keratinocyte conditioned medium (67.5 ml) was diluted with water to adjust the salt concentration to 0.1 M and manually passed over 0.5 ml of washed heparin-agarose beads (Sigma Chemical Co.). The column was then washed with 6 ml solution A containing 50 ug/ml BSA (hereinafter, solution A+BSA) and heparinagarose-bound material was eluted from the column with the stepwise application of 1.5 ml volumes of solution A+BSA containing 0.15, 1.0 and 2.0 M NaCl, respectively. The three elution fractions were collected separately, aliquoted, and frozen at $-80°$ C. for use in experiments. KAF activity was eluted from the column with increased NaCl concentrations.

Figure 7:
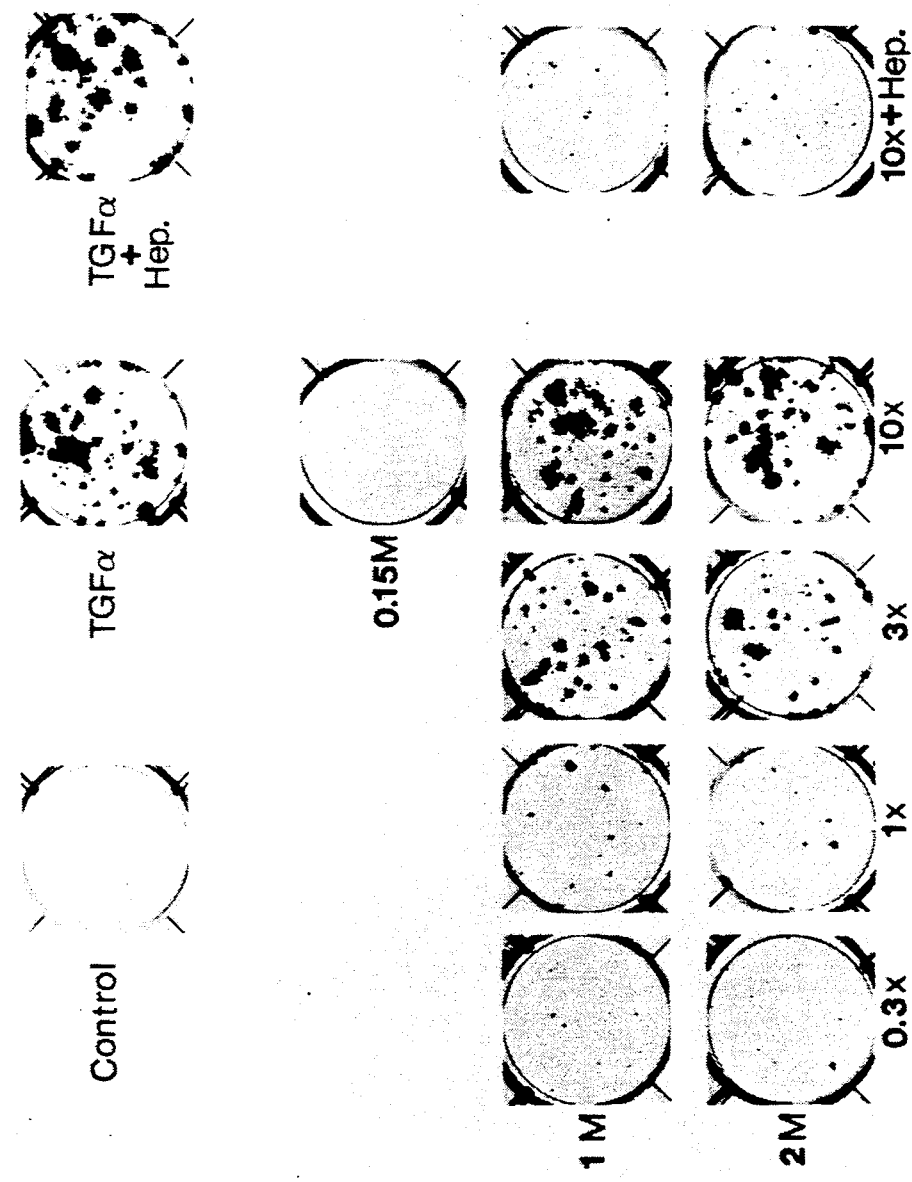
FIG. 7 shows the effect of KAF fractions eluted from heparin-agarose on the growth of human keratinocytes.

FIG. 7 shows that KAF stimulation of clonal growth of human keratinocytes can be used to assess KAF-containing fractions. The "control" shown in FIG. 7 represents keratinocytes plated in KGM medium for 20 hours and then cultured in KBM medium supplemented with hydrocortisone ($5 \times 10^{-7}$ M) and insulin (5 ug/ml). Under these conditions, little growth occurred. Similarly prepared cultures were treated with eluants from the heparin-agarose column at concentrations from $0.3 \times$ to $10 \times$ the original conditioned medium concentration. Clonal growth was stimulated by both the 1.0 m and 2.0 M eluants and this was inhibited by heparin, also as shown in FIG. 7. No KAF activity eluted in the 0.15 M NaCl fraction. TGF-alpha also stimulated clonal growth in these cultures, but this activity was not inhibited by heparin.

KAF from the 1 M or 2 M NaCl eluates as described above stimulated DNA synthesis in cultures of mouse AKR-2B cells cultured in MCDB 402 medium supplemented with 500 ng/ml insulin using the procedure of Shipley, G.D., *J Tiss Cult Meth* (1986) 10:117-123, incorporated herein by reference, which described the assay for determination of other growth factors. Stimulation of DNA synthesis in AKR-2B cells by KAF was completely inhibited by the addition of 10 ug/ml heparin sulfate (FIG. 8b, see arrow). No other known purified growth factors are inhibited by heparin in this assay or in the other assays shown here.

Thus, these assays when used in the presence and absence of heparin, as described herein, are useful in tracking the purification of KAF. (The same assays are also useful in the discovery of other molecules which have the ability to inhibit KAF as shown herein.) At the same concentrations as capable to stimulate AKR-2B cell growth, KAF was unable to stimulate DNA synthesis in normal human fibroblasts or in EGF-receptor-less mouse NR6 cells under similar conditions. bFGF was used as a positive control in these determinations. FIGS. 8, 8A, 8B and 8C show these results.

Figure 8A:
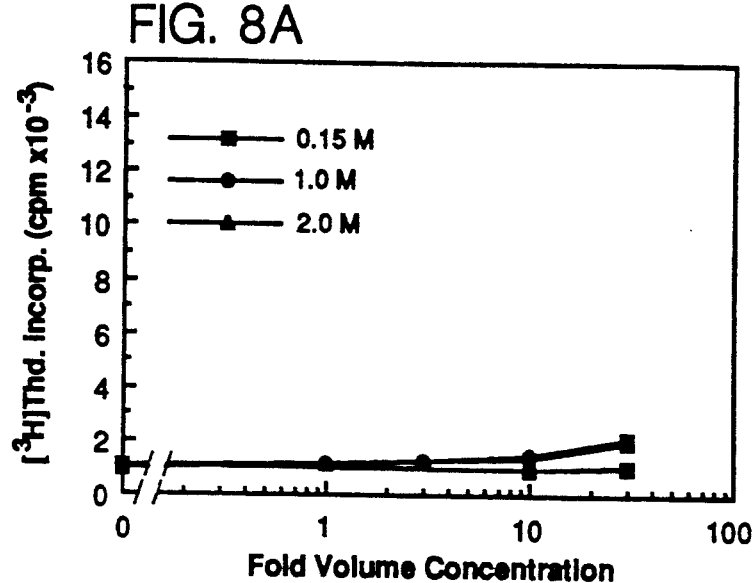
FIGS. 8A, 8B, and 8C compare the effect of KAF-containing fractions on the DNA uptake of neonatal foreskin fibroblast cells, AKR-2B cells, and murine NR-6 cells.
Figure 8B:
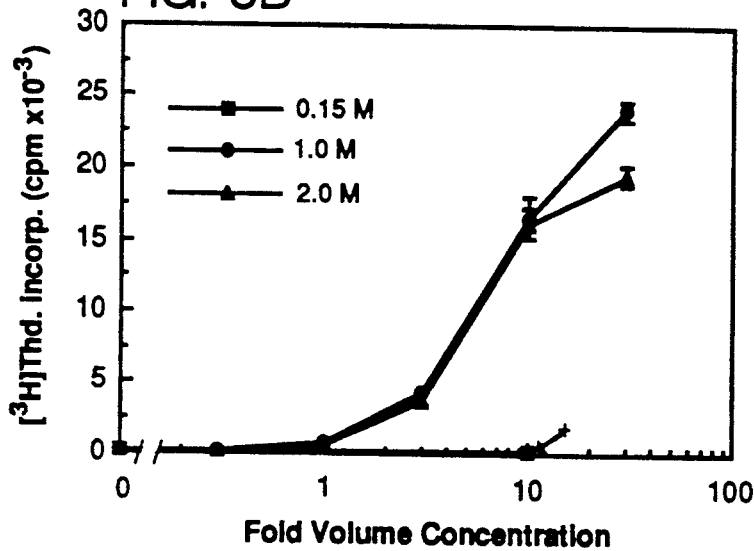
Figure 8C:
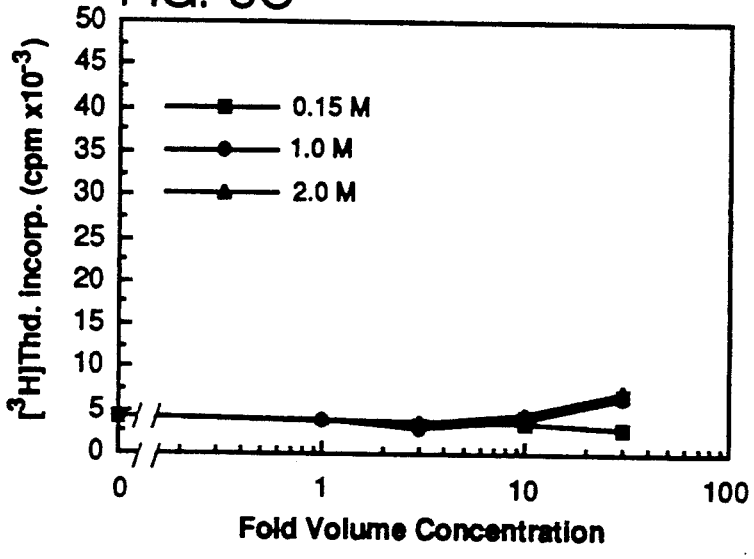

FIG. 8A shows the results obtained for the indicated fractions, normal human fibroblasts; FIG. 8B, using AKR-2B cells, and FIG. 8C using NR6 cells. Only AKR-2B cells are responsive to the KAF-containing 1M and 2M salt fractions. These results led us to use the AKR-2B cell thymidine incorporation assay to purify KAF from keratinocyte conditioned medium.

EXAMPLE 3

Isolation of Pure KAF

Keratinocytes were plated initially in medium KGM (Clonetics Corporation, San Diego, Calif.) at a density of approximately $2 \times 10^3$ cells/cm$^2$. The keratinocytes were grown in medium KGM for 2 to 3 days until rapidly proliferating cultures were obtained. The cultures were washed thoroughly with solution A and the medium replaced with medium KBM (Clonetics Corporation, San Diego, Calif.) supplemented only with $5 \times 10^{-7}$ M hydrocortisone (0.25 ml/cm$^2$). (Other supplementation such as insulin or EGF may also be used.) The cells were grown for 24 hours and then the medium was collected and discarded. The cell cultures received fresh KBM medium supplemented with hydrocortisone and the cultures were then allowed to grow with medium changes every 48 hours initially and every 24 hours once the cells reached high density. Except for the first medium change which was discarded, all of the conditioned medium from keratinocyte cultures was stored frozen at −20° C. until processed as described below.

Frozen keratinocyte conditioned medium was thawed and pooled in 9-18 liter batches and high molecular weight material in the medium was precipitated by adding zinc sulfate to a final concentration of 0.1 M. The high molecular weight precipitate was concentrated by centrifugation. The resulting precipitates were resuspended in 0.5 M EDTA (pH 7.4), suspensions from several centrifuge bottles combined, and the resuspended precipitate was extensively dialyzed against 1% acetic acid utilizing Spectropor dialysis tubing (3,500 M.W. cutoff). The dialyzed material was concentrated to a smaller volume (150-300 ml) by using centrifugal filtration concentration devices (Centricon-10, Amicon). The concentrated material was subsequently lyophilized to dryness and stored at −20° C. until use.

The lyophilized material was resuspended in a HEPES buffered saline solution (0.02 M HEPES, 0.1 M NaCl, $3.3 \times 10^{-6}$ M phenol red, pH 7.0) and the pH was readjusted to approximately 7.0-7.4 with NaOH as required. HEPES buffer as described above but containing no NaCl was then added to the solution to adjust the final salt concentration to approximately 0.1 M. The final volume of resuspended high molecular weight keratinocyte-derived conditioned medium material from 10 liters of conditioned medium was approximately 75-100 ml.

Batches of resuspended conditioned medium material were passed twice over a 1.0 ml column of heparin-acrylamide beads (Sigma Chemical Company, St. Louis, Mo.) at a flow rate of 0.8 ml/min. The heparin-acrylamide column was then washed for 20 minutes with HEPES-saline buffer at a flow rate of 0.5 ml/min. After the wash period, heparin-acrylamide bound material was eluted in a continuous NaCl gradient (0.1-3.0 M NaCl) in 0.02 M HEPES, pH 7.0. The total volume of the gradient elution was 10 ml. The flow rate through the column was 0.5 ml/min. and 0.5 ml fractions were collected.

A small portion of each fraction was diluted in solution A containing 50 ug/ml bovine serum albumin (BSA) as a carrier protein and the diluted material was tested for mitogenic activity in the AKR-2B thymidine incorporation assay described above.

Figure 9A:
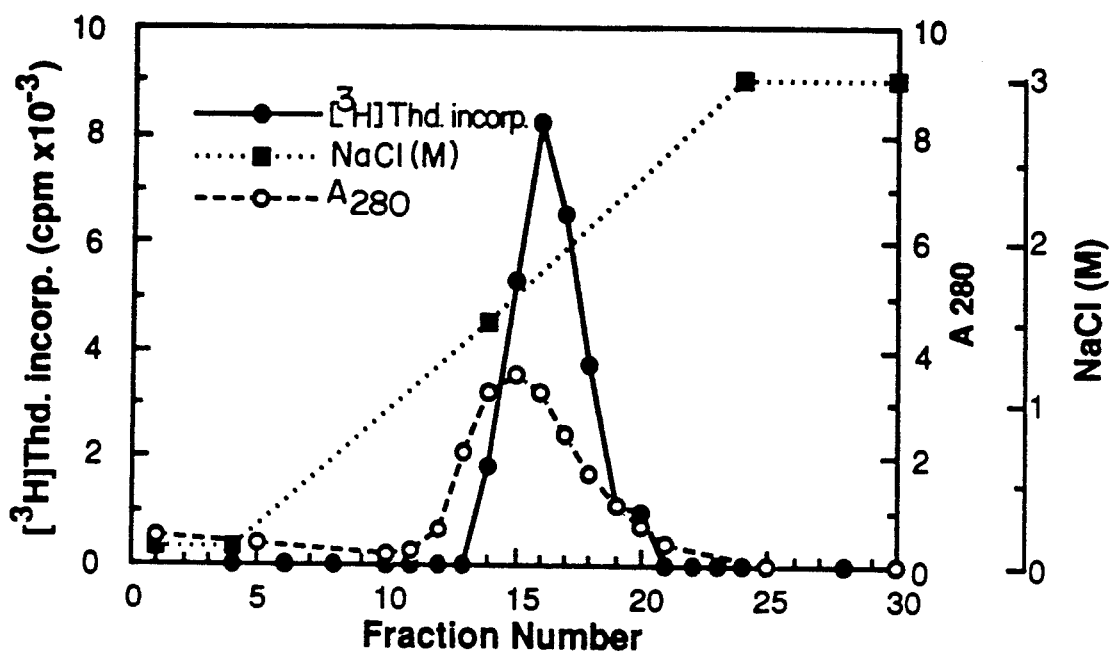
FIG. 9A shows a typical KAF elution profile.

A typical elution profile is shown in FIG. 9A. The peak of KAF mitogenic activity eluted at approximately 1.75 M NaCl.

Figure 9B:
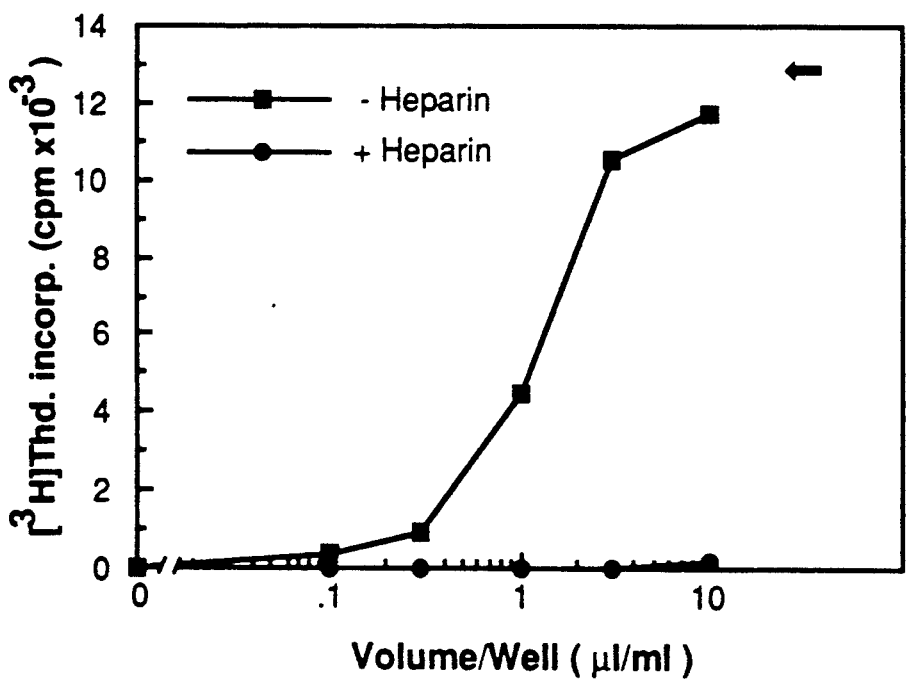
FIG. 9B shows thymidine incorporation activity with and without heparin addition.

The peak fractions from 5 separate heparin-acrylamide purification runs performed essentially as described for figure 9A, representing 65.5 liters of keratinocyte conditioned medium, were pooled. The volume was reduced using filtration with Centricon-10 (Amicon) and the final volume was adjusted to 2.5 ml with 0.02 M HEPES (pH 7.0). The pooled material was tested in the AKR-2B thymidine incorporation assay with and without the addition of 10 ug/ml heparin sulfate as shown in FIG. 9B. As previously demonstrated (FIG. 8B), KAF purified by heparin-affinity chromatography is a potent simulator of DNA synthesis in mouse AKR-2B cells and this mitogenic activity is blocked by the addition of 10 ug/ml heparin sulfate to the culture medium.

The amount of KAF mitogenic activity is quantified by comparison to an external standard. One unit of KAF activity is defined as the amount of material required to achieve ½ of the maximal mitogenic stimulation which can be induced by the addition of 10 ng/ml EGF to AKR-2B cells in the presence of 500 ng/ml insulin (indicated in Figure9b by the arrow). Based on this estimation, the amount of KAF activity that was obtained from 65.5 liters of keratinocyte conditioned medium was 25,939 units.

Figure 9C:
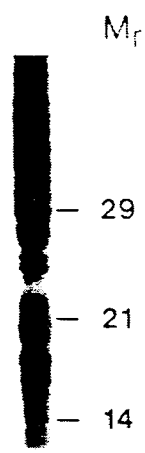
FIG. 9C shows an assessment of pooled KAF activity.

Pooled KAF activity isolated by heparinacrylamide chromatography (300 units) was analyzed by SDS-PAGE under nonreducing conditions followed by silver staining as shown in FIG. 9C. This analysis demonstrates that numerous proteins are present in the heparin-acrylamide purified material.

Figure 10A:
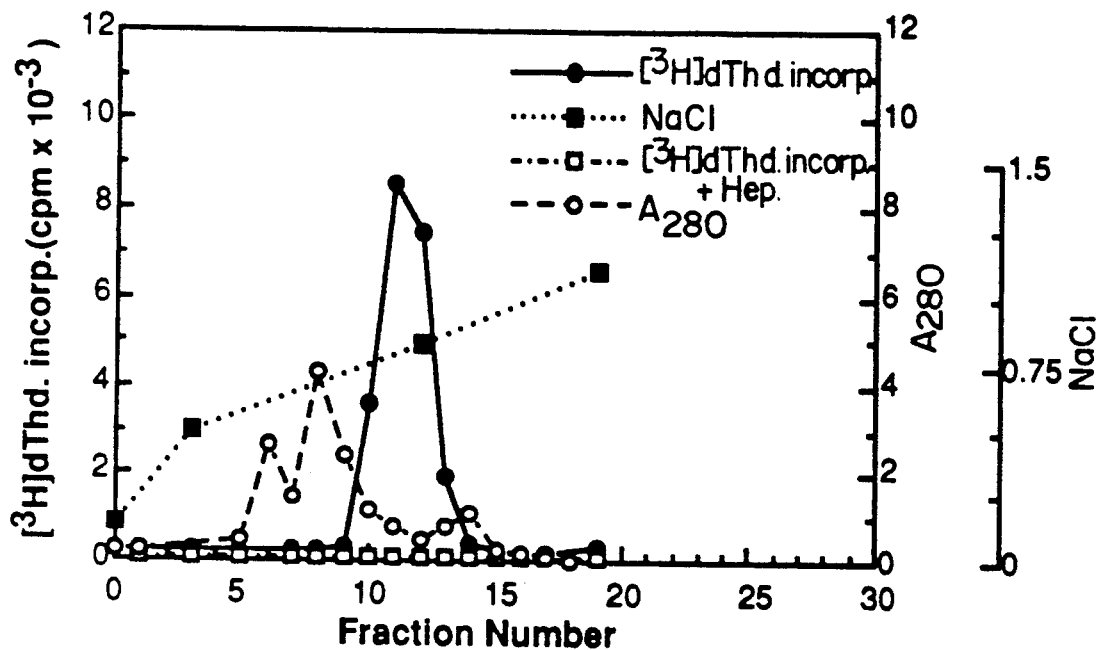

KAF was further purified by ion exchange chromatography on a mono-S cation exchange column (Pharmacia). Heparin-acrylamide purified KAF was applied to a mono-S exchange column in 0.02 M HEPES buffer containing 0.15 M NaCl (pH 7.0). The column was eluted in the same buffer with an increasing concentration gradient of NaCl as shown in FIG. 10A. The flow rate was 0.5 ml/min. and 0.5 ml fractions were collected. A portion of each fraction was diluted in saline solution A+BSA and tested in the AKR-2B cell thymidine incorporation assay as described above, either in the presence or absence of 10 ug/ml heparin sulfate. The results of this assay are shown in FIG. 10A. The peak of KAF mitogenic activity eluted from the mono-S column at approximately 0.8 M NaCl.

Approximately 16,500 units of KAF activity were recovered from fractions 10-12. Equal volumes from fractions 9-14 were analyzed by SDS-PAGE and subsequent silver staining. The volume loaded from fraction 11 contained 300 units of KAF mitogenic activity. Analysis of this SDS-PAGE under nonreducing conditions (FIG. 10B) indicated that a protein which migrated with an approximate molecular weight of 19,700 daltons correlated with KAF mitogenic activity.

Figure 10C:
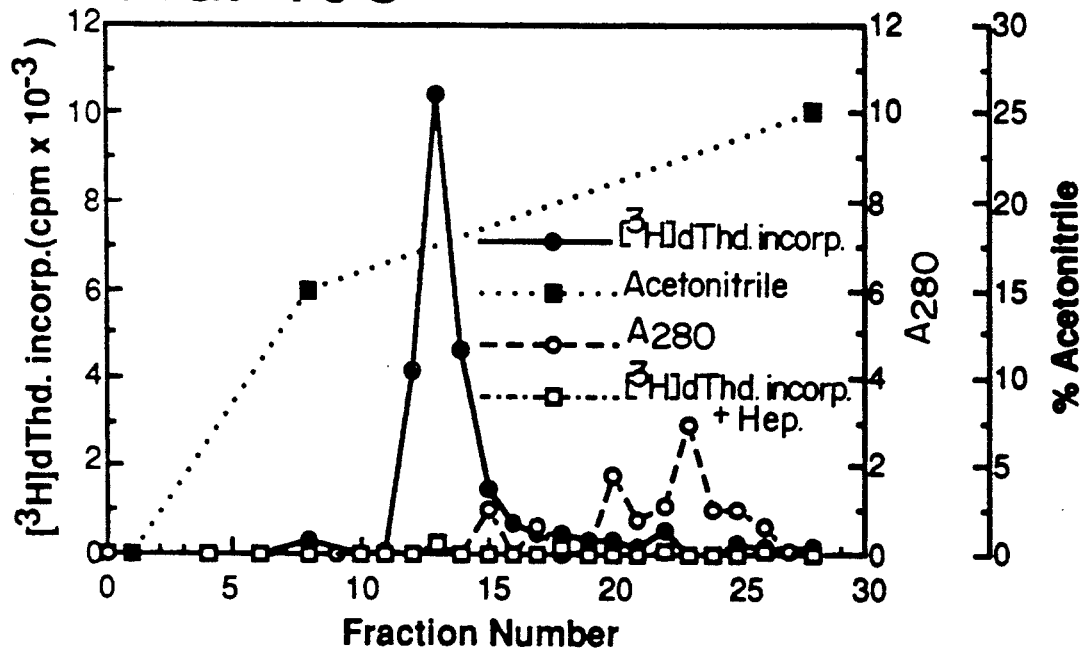

KAF purified by mono-S cation exchange chromatography was further purified by reverse-phase chromatography using a C-8 column (Pharmacia). Peak fractions 10, 11 and 12 from the cation exchange column shown in FIG. 10a were pooled and diluted to a final volume of 3.0 ml with 0.1% TFA in water. The sample was applied to a C-8 column, and the column subsequently washed with 10 ml of 0.1% TFA at a flow rate of 0.5 ml/min. After washing, a gradient of acetonitrile in 0.1% TFA and water was applied to the column at a flow rate of 0.5 ml/min. as shown in FIG. 10C. Fractions (0.5 ml) were collected. A small portion of each fraction was diluted in solution A+BSA and tested for mitogenic activity in the AKR-2B cell thymidine incorporation assay as described above. The results of the thymidine incorporation assay are shown in FIG. 10C. Heparin-inhibitable KAF mitogenic activity eluted from the C-8 column at approximately 18% acetonitrile. Equal volumes of fractions 11 through 17 were subjected to SDS-PAGE followed by silver staining (FIG. 10D). In addition, the same volumes of fractions 12 and 13 were analyzed by SDS-PAGE after reduction with dithiothreitol (FIG. 10D). Analysis of the data shown in FIG. 10d, demonstrated that a protein which migrates with an approximate molecular weight of 19,700 daltons under nonreducing conditions and 18,500 daltons under reducing conditions correlates with KAF biological activity.

Reversed phase purified KAF activity was further purified by C-8 reversed phase chromatography utilizing a shallow acetonitrile gradient (FIG. 10E). KAF activity from fraction 13 of FIG. 10c was lyophylized and resuspended in 0.1% TFA. The KAF preparation was applied to a C-8 reversed phase column and the column was eluted with a shallow gradient of acetonitrile in 0.1% TFA and water (0–15% acetonitrile in 7.5 min., 0.5 ml/min; followed by 15–26.5% acetonitrile in 94 minutes, 0.25 ml/min.). Fractions (0.25 ml) were collected every minute. A small portion from each fraction was diluted in solution A+BSA and tested in the AKR-2B cell thymidine incorporation assay as described above. The results are shown in FIG. 10e. Equal volumes of fractions 19–26 were subjected to SDS-PAGE and silver staining as previously described. The results are shown in FIG. 10F.

The results indicated that a protein which migrates in SDS-PAGE under reducing conditions with an apparent molecular weight of approximately 18,500 daltons is responsible for KAF activity. The streaking in the SDS-PAGE analysis at molecular weights slightly higher than 18,500 could be due to differential glycosylation of the KAF protein. Likewise, the protein band apparent in the peak fractions which migrates in SDS-PAGE at approximately 14,000 daltons could indicate a KAF species with less glycosylation.

EXAMPLE 4

Protein Microsequencing of KAF

Fractions 21 through 23 from the column chromatography shown in FIG. 10e were combined and lyophylized. The sample was resuspended in 0.1% TFA in water and aliquoted. A portion of the material was sequenced by automated Edman degradation and a portion was tested for biological activity in the AKR-2B cell thymidine incorporation assay. Analysis of the data obtained from protein microsequencing and from the AKR-2B thymidine incorporation assay indicated that 1 unit of KAF activity in the AKR-2B cell thymidine incorporation assay was equivalent to 0.14 picomoles of KAF peptide.

Protein microsequencing of the first twenty residues of KAF revealed that the KAF preparation contained two peptides, KAF-1 and KAF-2. Analysis of the data and comparison of the microsequence of KAF peptides to known protein sequences revealed a high degree of homology to a polypeptide growth factor termed amphiregulin (AR), a member of the EGF superfamily which includes epidermal growth factor (EGF) and transforming growth factor type-alpha (TGF-alpha) (see Background section). Both KAF and AR have forms that are truncated at the amino terminus by six amino acids (FIG. 11). The data suggest that AR and KAF are highly related if not identical proteins.

EXAMPLE 5

Molecular Cloning of a KAF cDNA

A cDNA was isolated from keratinocyte mRNA using oligonucleotide primers coding for 5' and 3' regions of AR (Plowman et al., *Mol Cell Biol* (1990) 10:1969-1981) as shown in FIG. 12. Human keratinocytes were grown in the same conditions utilized to isolate KAF protein (medium KBM supplemented with hydrocortisone). Poly-A+ RNA was isolated as previously described (Sternfeld et al., *J Cell Physiol* (1988) 136:297–304; Schwab et al., *Nature* (1984) 303:497–501). cDNA was synthesized from poly A+ RNA using reverse transcriptase and oligo-dT primers. The cDNA was amplified using the polymerase chain reaction (PCR) technique and the PCR-derived product was subsequently cloned into pTZ19U for synthesis of antisense cRNA probes for Northern blot analysis, and in vectors M13-19 and M13-18 for sequencing. The PCR amplified product was approximately 900 basepairs (bp) long which is in agreement with the predicted length of an AR cDNA amplified with these primers (888 bp). Subsequent restriction endonuclease and DNA sequence analysis (FIG. 12) revealed that the PCR product obtained coded for AR.

Figure 13:
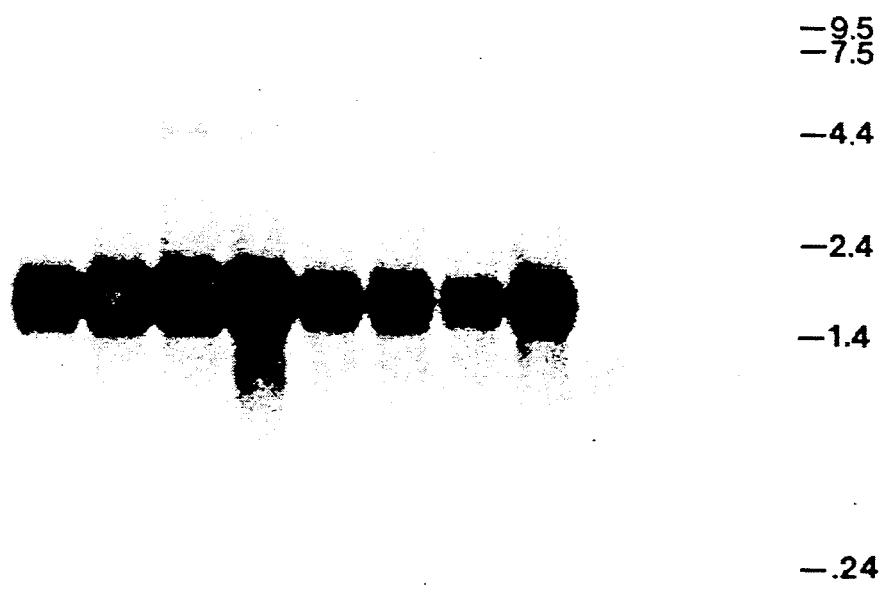
FIG. 13 shows the results of Northern blot analysis from various cell cultures.

Northern blot analysis of poly A+ RNA isolated from human keratinocytes cultured from several different individuals revealed a highly abundant 1.7 kilobase RNA in these cells which hybridizes to the antisense probe synthesized from pTZ19-AR1 (FIG. 13, lanes C-I). These results demonstrate that cultured human keratinocytes contain abundant mRNA coding for AR and support the hypothesis that AR and KAF are very similar if not identical molecules. Neither mRNA isolated from cultured normal human fibroblasts (lane A) nor from cultured normal human melanocytes (lane B) grown in serum-free medium exhibited the levels of KAF/AR gene expression seen in the mRNA isolated from keratinocyte cultures. This was true of the melanocyte cultures even though they were treated continuously with the phorbol ester, PMA, an agent known to induce the expression of the AR gene in some cultured human mammary carcinoma cells (Plowman et al., *Mol Cell Biol* (1990) 10:1969–1981).

In addition to the high levels of expression in keratinocyte cultures, the results in FIG. 13, lane J demonstrate for the first time that normal human mammary epithelial cells grown in a serum-free medium (Hammond et a., *Proc Natl Acad .Sci USA* (1984) 81:5435–5439) have high levels of mRNA coding for KAF/AR. This indicates that KAF/AR may be an autocrine growth factor for normal mammary epithelial cells as well as for keratinocytes and that the culture system used for these studies is useful for the identification of pharmaceutical agents that can regulate the expression of the KAF/AR gene in normal human mammary epithelial cells.

Unlike the normal mammary epithelial cells, mRNA isolated from a continuous mammary epithelial cell line (HBL100) did not contain high levels of KAF/AR mRNA (lane K), nor did two mammary tumor cell lines grown in culture in the absence of PMA (HS578T-lane L; BT474lane M).

In addition to these results, other studies have shown that KAF/AR mRNA levels in normal keratinocytes are not elevated by PMA treatment, and that in comparison to normal human keratinocytes, the mouse MK-2 cell line does not contain detectable levels of KAF/AR mRNA.

EXAMPLE 6

Stimulation of Keratinocyte Clonal Growth by KAF

Figure 14:
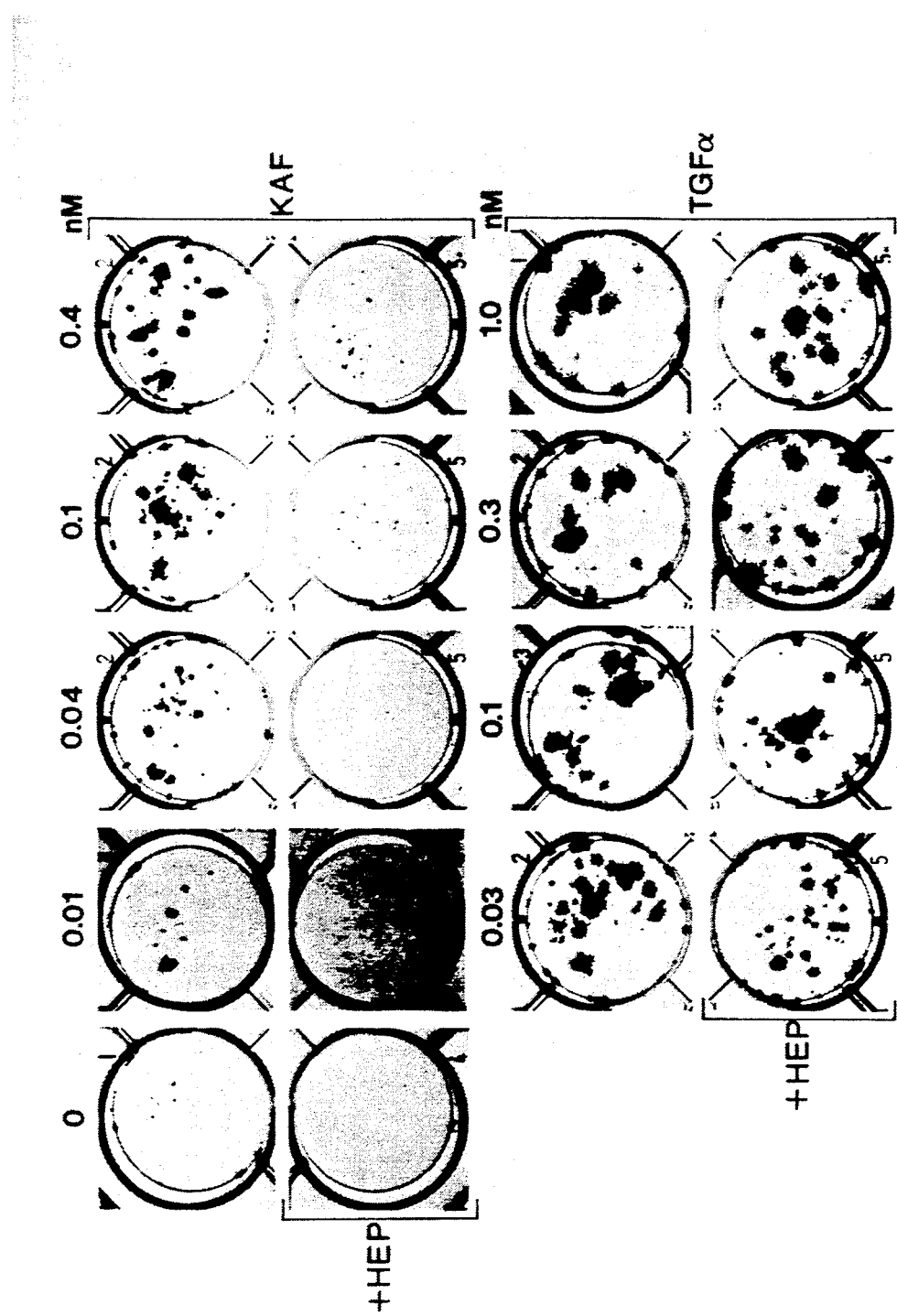
FIG. 14 shows the effect of KAF and TGF-alpha on clonal growth of human keratinocytes.

Purified KAF stimulated the clonal growth of normal human keratinocytes. Keratinocytes were plated at clonal densities as described above and grown in medium KBM supplemented with hydrocortisone, insulin and the indicated concentration of KAF or TGF-alpha with or without the addition of 30 ug/ml heparin sulfate as indicated in FIG. 14.

Purified KAF stimulates the clonal growth of these cells at low concentrations and the activity is inhibited by the addition of heparin sulfate at 30 ug/ml (+HEP) to the culture medium. At similar concentrations, TGF-alpha also stimulated keratinocyte clonal growth, but this activity was not inhibited by heparin.

EXAMPLE 7

Differential Activity for Keratinocytes and Fibroblasts

Figure 15A:
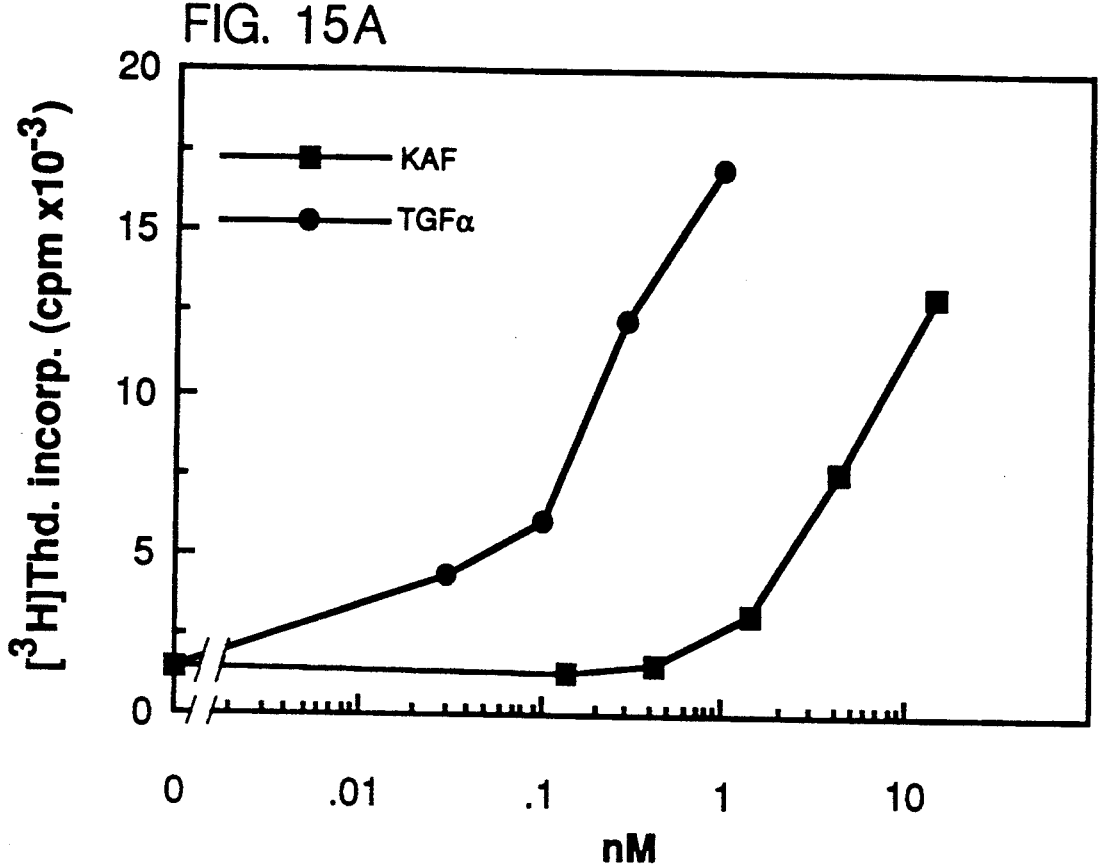
FIGS. 15A and 15B show the effect of KAF and other growth factors on fibroblast growth.
Figure 15B:
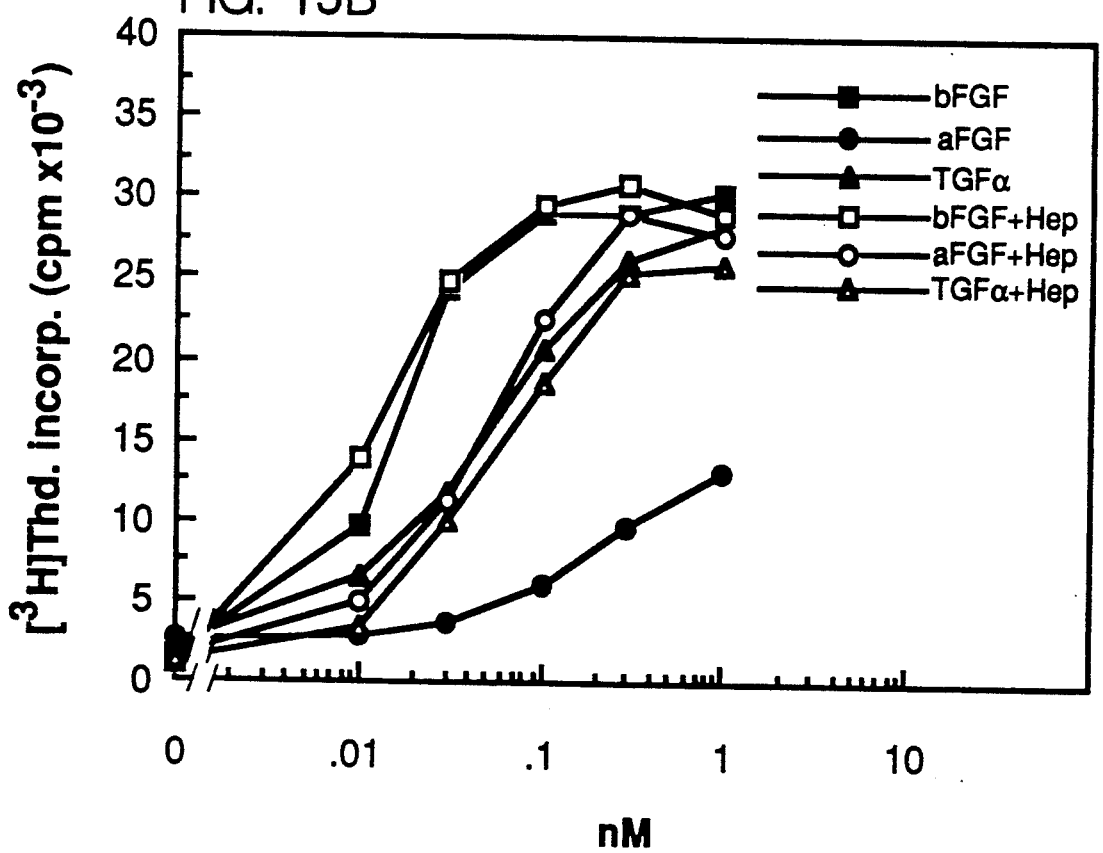

As set forth above, partially purified KAF (FIG. 8B) or purified (FIG. 2A) stimulated DNA synthesis in the AKR-2B cell thymidine incorporation assay and the mitogenic activity of KAF was nearly identical to the activity of TGF-alpha. The ability of KAF to stimulate DNA synthesis in AKR-2B cells (FIG. 2A) correlates with the ability of KAF to stimulate the growth of human keratinocytes (FIG. 14). However, when KAF was tested for the ability to stimulate DNA synthesis in human dermal fibroblasts, the concentration of KAF that was required to obtain a response was 30-50 fold higher than the effective concentration of TGF-alpha (FIG. 15A). Other heparin-binding growth factors (acidic and basic fibroblast growth factor, aFGF and bFGF) are also effective in stimulating DNA synthesis in human dermal fibroblasts (FIG. 15B), however, like TGF-alpha, the effective dose for these factors is significantly lower than the concentrations of KAF required to obtain a response in these cells.

The effective concentration of bFGF and aFGF for keratinocyte growth is similar to the effective concentration required to stimulate dermal fibroblasts (Shipley et al., *J Cell Physiol* (1989) 138:511-518). Thus, of factors known to effect the growth of both keratinocyte and fibroblast cell types, only KAF has a differential effect. In pharmaceutical preparations of growth factors, KAF would be an effective epidermal healing agent that would be less likely to stimulate the proliferation of fibroblasts in the underlying dermis causing scar formation.

Example 8

Differences Between Human Keratinocytes and Balb/c MK Cells

KAF stimulates DNA synthesis in mouse Balb/c MK keratinocyte cell line at high density but not at clonal density. The mouse keratinocyte-derived cell line, MK-2, has been used widely as a model of normal keratinocyte physiology. However, MK-2 cells are completely dependent on the presence of exogenously added EGF/TGF-alpha for proliferation at both low and high density, unlike human keratinocytes. Moreover, these cells do not synthesize KAF as do normal human keratinocytes. Nevertheless, KAF can stimulate DNA synthesis in high density cultures of MK cells and the effect of KAF is blocked by the addition of heparin sulfate as set forth above.

The Balb/c MK-2 mouse keratinocyte cell line was obtained from Dr. Bernard Weissman. These cells were routinely grown in medium KBM supplemented with 10 ug/ml Gentamicin sulfate, 5 ug/ml insulin, 10 ng/ml EGF and 0.5% FBS. This medium is referred to in the text as "MK medium." MK-2 cells were plated in 24 well tissue culture plates at a density of $3 \times 10^4$ cells/cm$^2$ in MK medium. After 72 hours of culture, each well was washed two times with solution A and 0.1 ml of MK medium without EGF supplementation was added to each well. The cells were cultured for an additional 24 hours and then the medium was replaced with MK medium without EGF. Growth factors were then added to the wells at the concentrations of 0.01-1 nM [$^3$H]thymidine (8 uCi/ml) was added to each well and the cells were cultured for 24 hours. After this culture period, incorporation of [$^3$H] thymidine in each experimental well was determined as described for AKR-2B cells above (Shipley, 1986), and enhanced incorporation was shown (FIG. 3).

Figure 16:
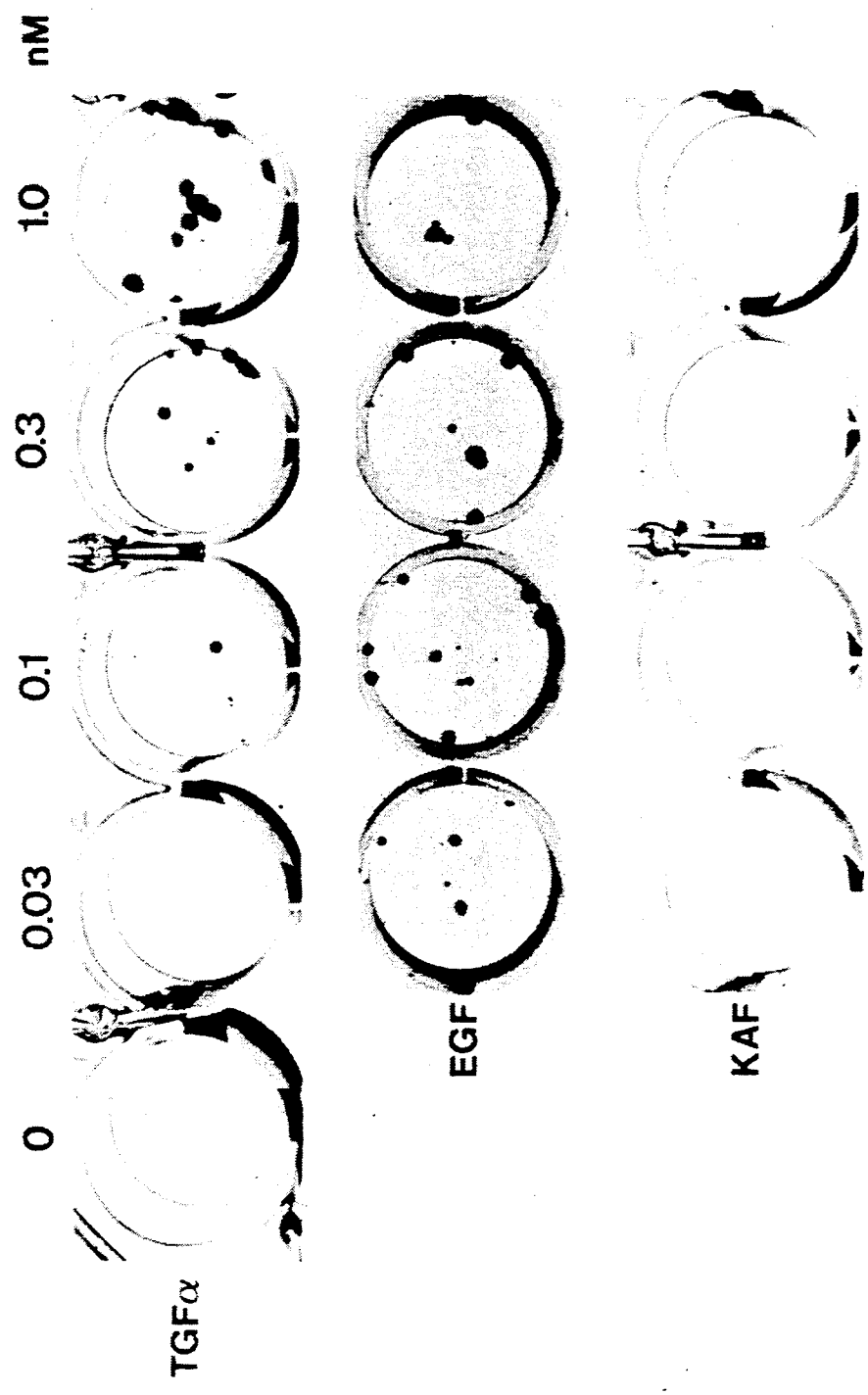
FIG. 16 shows a comparison of the activities of TGF-alpha, EGF and KAF on clonal growth of MK-2 cells.

Although purified KAF can replace EGF or TGF-alpha in stimulating DNA synthesis in MK-2 cells at high density, clonal growth of these cells is only supported by EGF or TGF-alpha and not by KAF (FIG. 16). Clonal growth of MK-2 cells was carried out utilizing a protocol similar to that described for human keratinocytes. Briefly, MK-2 cells were trypsinized from stock flasks, pelleted, resuspended in MK medium, and plated at 275 cells/well in 24 well plates. After 24 hours of culture each well was washed 2 times with solution A and 0.5 ml of MK medium without EGF was added to each well. Experimental factors were added to corresponding wells, at the concentrations shown in FIG. 16. After 10 days incubation, the colonies which developed were fixed in 10% formalin and stained with crystal violet for photography. As seen from these results, colonies appeared when TGF-alpha was added at 0.1-1 nM or when EGF was added from 0.03-1 nM; however, no colonies were formed in plates containing KAF in this range.

The ability of purified KAF to stimulate the formation of colonies in neonatal human keratinocytes was shown to be positive (FIG. 14) while KAF was inactive with a corresponding assay using BALB/c-MK cells.

EXAMPLE 9

Relationship to EGF

Figure 17A:
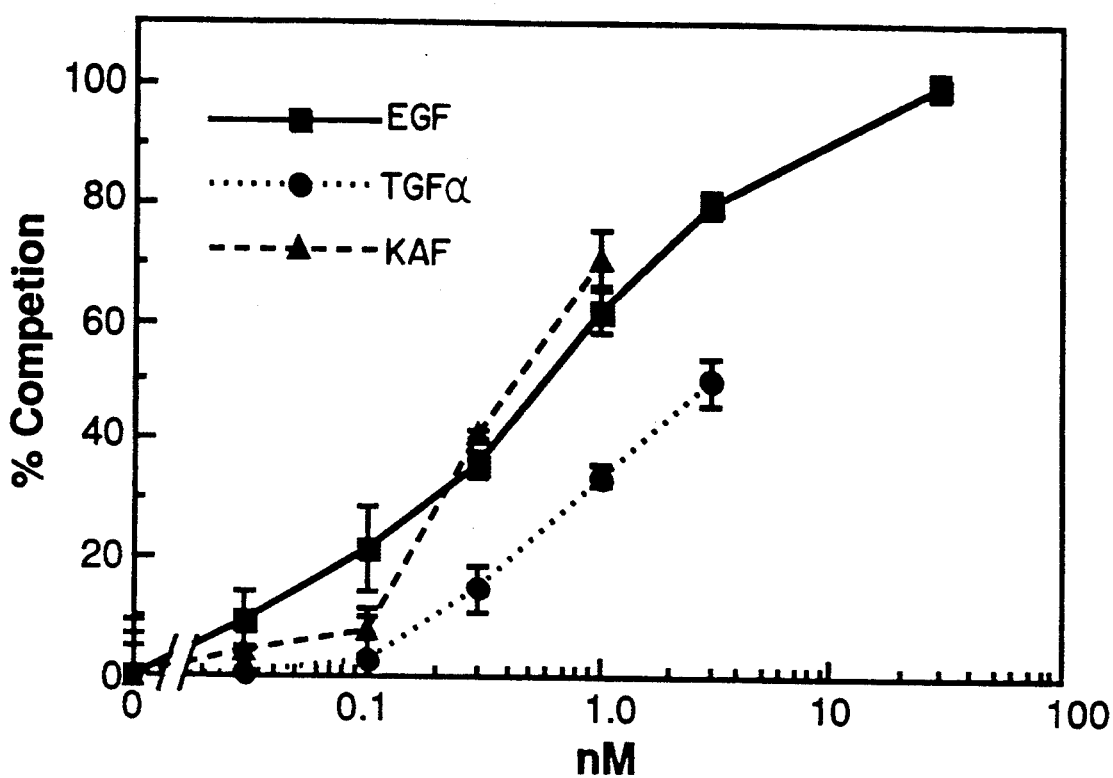
FIGS. 17A and 17B show competition of KAF, TGF-alpha and EGF for $^{125}$I-EGF binding and the effect of heparin thereon.
Figure 17B:
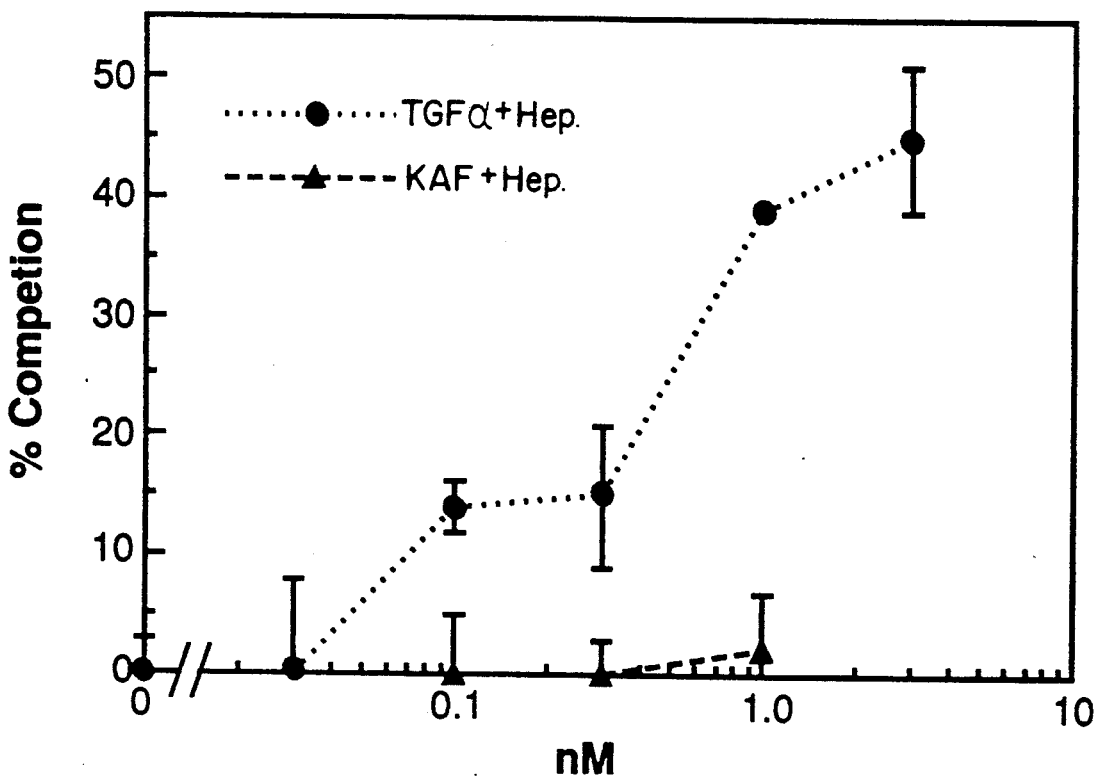

The possibility that KAF and EGF bind to the same receptor on AKR-2B cells was investigated as follows. The cells were grown as described for thymidine incorporation assays except that at the last medium change the cells received binding buffer (medium MCDB 402 buffered with 20 mM HEPES, pH 7.4, supplemented with 1.0 mg/ml BSA). The ability of KAF, TGF-alpha and EGF to compete with 50 pM $^{125}$I-EGF binding was determined at 4° C. 100% competition was determined by adding an excess of unlabeled EGF (>100 nM). As shown in FIGS. 17A and 17B, KAF as well as TGF-alpha and EGF competed for $^{125}$I-EGP binding to AKR-2B cells.

The ability of KAF to compete for binding was blocked by the addition of 10 ug/ml heparin sulfate to the binding medium (FIG. 17B), whereas binding competition by TGF-alpha (FIG. 17B) or EGF (not shown) was not changed by the addition of heparin. Thus, the ability of heparin sulfate and other sulfated compounds which inhibit KAF mitogenic activity may do so by blocking the ability of KAF to bind to its cell surface binding sites.

I claim:

1. A method to assess the ability of a candidate substance to inhibit or stimulate KAF production by KAF-producing cells, selected from the group consisting of normal human kerstinocytes, immortalized keratinocytes, and normal mammary epithelial cells, which method comprises culturing said KAF-producing cells in the presence of said candidate substance and comparing the quantity of KAF-mRNA and/or KAF-protein produced in said cultured cells as compared to a control culture of said KAF-producing cells wherein the candidate substance is absent.

2. The method of claim 1 wherein said KAF-mRNA and/or KAF-protein is detected by hybridization to a cRNA or cDNA probe encoding KAF or a portion thereof.

* * * * *